(12) United States Patent
Eberle et al.

(10) Patent No.: US 7,385,061 B2
(45) Date of Patent: Jun. 10, 2008

(54) FURAZANOBENZIMIDAZOLES

(75) Inventors: Martin Eberle, Bottmingen (CH); Felix Bachmann, Basel (CH); Alessandro Strebel, Oberwil (CH); Subho Roy, West Bengal (IN); Sudhir Srivastava, Uttar Pradesh (IN); Goutam Saha, West Bengal (IN)

(73) Assignee: Basilea Pharmaceutica AG, Basel (CH)

( * ) Notice: Subject to any disclaimer, the term of this patent is extended or adjusted under 35 U.S.C. 154(b) by 0 days.

(21) Appl. No.: 10/557,539

(22) PCT Filed: May 19, 2004

(86) PCT No.: PCT/IB2004/001723

§ 371 (c)(1),
(2), (4) Date: Nov. 21, 2005

(87) PCT Pub. No.: WO2004/103994

PCT Pub. Date: Dec. 2, 2004

(65) Prior Publication Data
US 2007/0043061 A1 Feb. 22, 2007

(30) Foreign Application Priority Data
May 23, 2003 (EP) .................................. 03405365

(51) Int. Cl.
A61K 31/4245 (2006.01)
C07D 413/04 (2006.01)

(52) U.S. Cl. ...................................... 548/125; 514/364
(58) Field of Classification Search ................. 548/125
See application file for complete search history.

(56) References Cited
U.S. PATENT DOCUMENTS
2004/0034037 A1* 2/2004 Harbeson et al. ...... 514/255.05
2004/0214817 A1 10/2004 Pierce et al.

FOREIGN PATENT DOCUMENTS
WO WO03/066629 A 8/2003

OTHER PUBLICATIONS
European Search Report dated Oct. 13, 2003.
International Search Report dated Sep. 20, 2004.
Database Chemcats Online Chemical Abstracts Service, Columbus, Ohio, US, XP002257449, Apr. 30, 2003.
Database Chemcats Online, Chemical Abstracts Service, Columbus, Ohio, US, XP002257450, May 19, 2003.
Database Chemcats Online, Chemical Abstracts Service, Columbus, Ohio, US, XP002257451, Apr. 29, 2003.
Sergievskii A V et al: "4-Aminofurazan-3-Carvoxylic Acid Iminoester in Reactions with N,O-Nucelphiles" Russian Journal of Organic Chemistry, Consultants Bureau, US, vol. 38, No. 6, 2002, pp. 872-874.
Sergievskii A V et al: "Reactions of Methyl 4-Aminofurazan-3-Carboximidate With Nitrogen-Containing Nucleophiles", Russian Journal of Organic Chemistry, Consultants Bureau, US, vol. 37, No. 5, 2001, pp. 717-720.
DE 31 00 771 A (USV Pharma Corp) Aug. 26, 1982.

* cited by examiner

Primary Examiner—Laura L Stockton

(57) ABSTRACT

The invention relates to compounds of formula (I) wherein R represents aryl or heteroaryl, X is oxygen, a carbonyl group, an oxime derivative of a carbonyl group or an $\alpha,\beta$-unsaturated carbonyl group, and the substituents $R^1$ to $R^6$ have the meanings given in the specification, for use as medicaments, to novel compounds of formula (I), to methods of synthesis of such compounds, to pharmaceutical compositions containing compounds of formula (I), to the use of a compounds of formula (I) for the preparation of a pharmaceutical composition for the treatment of neoplastic and autoimmune diseases, and to methods of treatment of neoplastic and autoimmune diseases using such compounds of formula (I) or of pharmaceutical compositions containing same

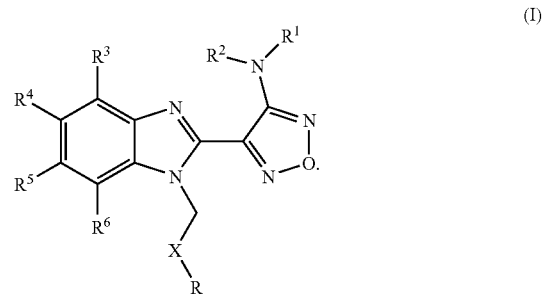

17 Claims, No Drawings

FURAZANOBENZIMIDAZOLES

The invention relates to novel substituted furazanobenzimidazoles, processes for the preparation thereof, pharmaceutical compositions containing same, the use thereof optionally in combination with one or more other pharmaceutically active compounds for the therapy of neoplastic diseases and autoimmune diseases, and a method for the treatment of such a diseases.

BACKGROUND OF THE INVENTION

Cancer is one of the leading causes of death in humans. Although a variety of drugs against neoplastic diseases have been developed and techniques are available such as surgery and radiation therapy, there is still a need for alternative and improved methods of treatment of neoplastic diseases.

Autoimmune diseases are associated with abnormal lymphoproliferation as a result of defects in the termination of lymphocyte activation and growth. Often, such diseases are associated with inflammation like rheumatoid arthritis, insulin dependent diabetes mellitus, multiple sclerosis, systemic lupus erythematosus and the like. The treatment of such diseases is focused on anti-inflammatory and immunosuppressive drugs which in numerous cases show severe side effects. Hence, there is a need for alternative drugs with a new mode of action showing less side effects.

Apoptosis is a term used to describe a series of cellular events which occur to bring about programmed cell death. There are various apoptotic pathways, some of which have been characterized, whereas others remain to be elucidated. If the balance between cell division and apoptosis is disturbed, life-threatening diseases including cancer, autoimmune disorders, neurodegenerative and cardiovascular diseases may occur.

In recent years it has become evident that programmed cell death (apoptosis) is as important to the health of a multicellular organism as cell division. By repeated cell division and differentiation throughout development or tissue repair, surplus or even harmful cells are generated. In order to maintain tissue homeostasis these cells have to be removed or killed. The delicate interplay between cell growth and apoptosis in an organism is mirrored in the complex molecular balance that determines whether an individual cell undergoes division, arrests in the cell cycle or commits to programmed cell death.

Dysregulation of cell proliferation, or lack of appropriate cell death, has wide ranging clinical implications. A number of diseases associated with such dysregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like. Such cells may lose the normal regulatory control of cell division, and may also fail to undergo appropriate cell death.

As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or re-established in epithelial cells, in endothelial cells, in muscle cells, and in others which have lost contact with extracellular matrix. These cells are potentially able to colonize other organs and therefore can develop into pathologies like neoplasias, endometriosis and the like.

Recently, a patent application was published disclosing a number of structurally related compounds (WO 03/066629). These compounds are described as being inhibitors of GSK-3 and LCK kinase, but have no relevance in apoptosis and medical conditions connected therewith.

SUMMARY OF THE INVENTION

Furazanobenzimidazoles of formula (I) are selectively inducing apoptosis in cancer cells, and can be used for the treatment of neoplastic and autoimmune diseases. The invention relates to compounds of formula (I), in particular to such compounds for use as medicaments, to methods of synthesis of such compounds, to pharmaceutical compositions containing compounds of formula (I), to the use of a compounds of formula (I) for the preparation of a pharmaceutical composition for the treatment of neoplastic and autoimmune diseases, and to methods of treatment of neoplastic and autoimmune diseases using such compounds of formula (I) or of pharmaceutical compositions containing same.

DETAILED DESCRIPTION OF THE INVENTION

The invention relates to compounds of formula (I)

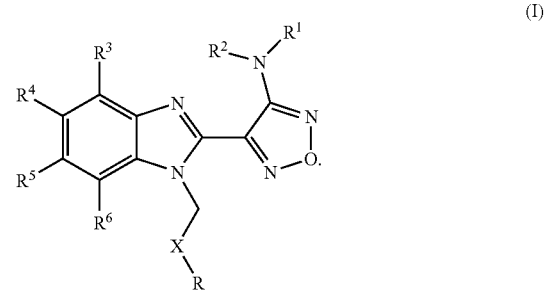

wherein

R represents aryl or heteroaryl optionally substituted by up to four substituents independently selected from alkyl, cycloalkyl, cycloalkyl-lower alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, cycloalkoxy, halo-lower alkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkylcarbonyloxy, amino, monoalkylamino, dialkylamino, aminocarbonylamino wherein each of the two amino groups is optionally substituted by alkyl, alkenyl, alkinyl or alkoxy-lower alkyl, heterocyclylcarbonylamino wherein heterocyclyl is bound via a nitrogen atom, aminosulfonylamino wherein each of the two amino groups is optionally substituted by alkyl, alkenyl, alkinyl or alkoxy-lower alkyl, heterocyclylsulfonylamino wherein heterocyclyl is bound via a nitrogen atom, lower alkoxycarbonylamino, lower alkylcarbonylamino wherein alkyl is optionally substituted by one or two substituents selected from optionally substituted phenyl, guanidyl, halogen, cyano, alkoxy, optionally substituted phenoxy, alkylmercapto and optionally substituted amino; lower alkenylcarbonylamino wherein alkenyl is optionally substituted by one or two substituents selected from lower alkyl, halo-lower alkyl, optionally substituted phenyl, halogen, cyano, alkoxy and optionally substituted amino; amino-lower alkyl or amino-lower alkylamino, wherein the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heterocyclyl, lower alkylcarbonyl, formyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, and nitro;

and wherein two adjacent substituents together with the atoms of aryl or heteroaryl may form a 5 or 6 membered carbocyclic or heterocyclic ring;

X represents oxygen; a group C=Y, wherein Y stands for oxygen or nitrogen substituted by hydroxy or alkoxy; or a group —CO—CH=CH— wherein the C=C bond is connected to R; $R^1$ and $R^2$, independently of each other, represent hydrogen, alkyl, cycloalkyl, cycloalkyl-alkyl, optionally substituted arylalkyl, optionally substituted heteroarylalkyl, hydroxyalkyl, alkoxyalkyl, hydroxyalkoxyalkyl, alkoxyalkoxyalkyl, cyanoalkyl, optionally substituted alkenyl, optionally substituted alkinyl, or lower alkylcarbonyl wherein lower alkyl is optionally substituted by one or two substitutents selected from aryl, optionally substituted amino, alkoxy and aryloxy, $R^3$, $R^4$, $R^5$ and $R^6$, independently of each other, represent hydrogen, lower alkyl, halo-lower alkyl, cycloalkyl, cycloalkyl-lower alkyl, hydroxy-lower alkyl, lower alkoxy-lower alkyl, lower alkoxy-lower alkoxy-lower alkyl, halo-lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, halo-lower alkoxy, cycloalkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, amino, carbamoyl, sulfamoyl, amino-lower alkyl or amino-lower alkylamino, wherein in each case the nitrogen atom is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heterocyclyl, lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, or nitro, or $R^3$ and $R^4$, $R^4$ and $R^5$, or $R^5$ and $R^6$ together with the atoms of the phenyl ring form a 5 or 6 membered carbocyclic or heterocyclic ring;

and salts thereof.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Double bonds in principle can have E- or Z-configuration. The compounds of this invention may therefore exist as isomeric mixtures or single isomers. If not specified both isomeric forms are intended.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula (I).

Alkyl has from 1 to 12, preferably from 1 to 7 carbon atoms, and is linear or branched. Alkyl is preferably lower alkyl.

Lower alkyl has 1 to 4 carbon atoms and is butyl, such as n-butyl, sec-butyl, isobutyl, tert-butyl, propyl, such as n-propyl or isopropyl, ethyl or methyl. Preferably lower alkyl is methyl or ethyl.

Cycloalkyl has preferably 3 to 7 ring carbon atoms, and may be unsubstituted or substituted, e.g. by lower alkyl or lower alkoxy. Cycloalkyl is, for example, cyclohexyl, cyclopentyl, or methylcyclopentyl.

Aryl stands for a mono- or bicyclic fused ring aromatic group with 5 to 10 carbon atoms, such as phenyl, 1-naphthyl or 2-naphthyl, or also a partially saturated bicyclic fused ring comprising a phenyl group, such as indanyl, dihydro- or tetrahydronaphthyl.

In optionally substituted phenyl, substituents are preferably lower alkyl, lower alkoxy, lower alkoxy-lower alkoxy, methylenedioxy, halo-lower alkyl, lower alkoxy-lower alkyl, halo, or nitro.

Heteroaryl represents an aromatic group containing at least one heteroatom selected from nitrogen, oxygen and sulfur, and is mono- or bicyclic. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include pyrrolyl, thienyl, furyl, pyrazolyl, imidazolyl, triazolyl, oxazolyl, isoxazolyl, oxadiazolyl, thiazolyl, isothiazolyl, thiadiazolyl, pyridyl, pyridazinyl, pyrimidinyl, pyrazinyl, benzo fused derivatives of such monocyclic heteroaryl groups, such as indolyl, benzimidazolyl or benzofuryl, quinolinyl, isoquinolinyl, quinazolinyl, or purinyl.

In optionally substituted heteroaryl, substituents are preferably lower alkyl, lower alkoxy, lower alkoxy-lower alkoxy, amino, optionally substituted by one or two substituents selected from lower alkyl, lower alkenyl and alkylcarbonyl, halo-lower alkyl, lower alkoxy-lower alkyl, halo, or nitro.

Alkenyl contains one or more, e.g. two or three, double bonds, and is preferably lower alkenyl, such as 1- or 2-butenyl, 1-propenyl, allyl or vinyl.

Alkinyl is preferably lower alkinyl, such as propargyl or acetylenyl.

In optionally substituted alkenyl or alkinyl, substituents are preferably lower alkyl, lower alkoxy, halo or di(lower alkyl)amino, and are connected with a saturated carbon atom of alkenyl or alkinyl or with an unsaturated carbon atom of alkenyl.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl and tetrahydropyranyl.

Acyl designates, for example, alkylcarbonyl, cyclohexylcarbonyl, arylcarbonyl, aryl-lower alkylcarbonyl, or heteroarylcarbonyl. Lower acyl is preferably lower alkylcarbonyl, in particular propionyl or acetyl.

Hydroxyalkyl is especially hydroxy-lower alkyl, preferably hydroxymethyl, 2-hydroxyethyl or 2-hydroxy-2-propyl.

Cyanoalkyl designates preferably cyanomethyl and cyanoethyl.

Haloalkyl is preferably fluoroalkyl, especially trifluoromethyl, 3,3,3-trifluoroethyl or pentafluoroethyl.

Halogen is fluorine, chlorine, bromine, or iodine.

Lower alkoxy is especially methoxy, ethoxy, isopropyloxy, or tert-butyloxy.

Arylalkyl includes aryl and alkyl as defined hereinbefore, and is e.g. benzyl, 1-phenethyl or 2-phenethyl.

Heteroarylalkyl includes heteroaryl and alkyl as defined hereinbefore, and is e.g. 2-, 3- or 4-pyridylmethyl, 1- or 2-pyrrolylmethyl, 1-pyrazolylmethyl, 1-imidazolylmethyl, 2-(1-imidazolyl)ethyl or 3-(1-imidazolyl)propyl.

Two adjacent substituents which together with the atoms of aryl or heteroaryl may form a 5 or 6 membered carbocyclic or heterocyclic ring are, for example, propylene, 1- or 2-oxopropylene, 1- or 2-oxapropylene, 1-oxapropylidene, methylenedioxy, difluoromethylenedioxy, 1- or 2-azapropylene, 1- or 2-azapropylidene, 1,2- or 1,3-diazapropylidene, 1,3-diaza-2-oxopropylene, butylene, 1- or 2-oxabutylene, ethylenedioxy, 1- or 2-azabutylene, or 1- or 2-azabutadienylidene, or such groups carrying further substituents as defined hereinbefore.

In substituted amino, the substituents are preferably those mentioned as substituents $R^1$ and $R^2$. In particular, substituted amino is alkylamino, dialkylamino, optionally substituted arylalkylamino, or lower alkylcarbonylamino, and also lower alkoxycarbonylamino or optionally substituted aminocarbonylamino.

When X represents a group C=Y, wherein Y stands for nitrogen substituted by hydroxy, this corresponds to an oxime function. Oximes and the corresponding oxime alkyl ethers (nitrogen substituted by alkoxy) may be present in E or Z form, or as mixture of isomers.

When X represents a group —CO—CH=CH— wherein the C=C bond is connected to R, R is connected to the terminal carbon atom of the C=C bond. The C=C bond may be present in E or Z form, preferably in E form.

Salts are especially the pharmaceutically acceptable salts of compounds of formula (I).

Such salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantane-carboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compound of the formula (I) may be administered in the form of a pro-drug which is broken down in the human or animal body to give a compound of the formula (I). Examples of pro-drugs include in vivo hydrolysable esters and amides of a compound of the formula (I). Particular pro-drugs considered are ester and amides of naturally occurring amino acids and ester or amides of small peptides, in particular small peptides consisting of up to five, preferably two or three amino acids as well as esters and amides of pegylated hydroxy acids, preferably hydroxy acetic acid and lactic acid. Pro-drug esters are formed from the acid function of the amino acid or the C terminal of the peptide and suitable hydroxy group(s) in the compound of formula (I). Pro-drug amides are formed from the amino function of the amino acid or the N terminal of the peptide and suitable carboxy group(s) in the compound of formula (I), or from the acid function of the amino acid or the C terminal of the peptide and suitable amino group(s) in the compound of formula (I).

The compounds of formula (I) have valuable pharmacological properties. The invention also relates to compounds of formula (I) as defined hereinbefore for use as medicaments.

The efficacy of the compounds of the invention in inducing apoptosis in tumor cells can be demonstrated as follows:

Relative fluorescent activities of suitable tumor cell lines transfected with green fluorescent protein (GFP) are measured in the presence of compounds of the invention and of standard tumor drugs, using the method described in WO 99/35493. Suitable tumor cell lines are A20.2J, a BALB/c B cell lymphoma, PB-3c, an IL-3 dependent, non tumorigenic mastocyte line isolated from the bone marrow of a DBA/2 mouse, Jurkat, a human acute T cell leukemia cell line, K562, a human chronic myelogenous leukemia cell line, HL60, a human acute promyelocytic leukemia cell line, Ramos and Raji, human B-cell lymphoma cell lines, H9 and Hut78, human T-cell lymphoma cell lines, HeLa and KB, human squamous cell carcinoma cell lines, MCF7, SK-BR-3, PC3, HBL-100, SW480, H460 and H1792, human adenocarcinoma cell lines and HT-1080, a human fibrosarcoma cell line.

Preferred standard drugs as compounds for comparisons are: a) antimetabolites such as 5-fluorouracil (ICN), gemcitabine HCl (Gemzar™, Eli Lilly), b) alkylating agents such as oxaliplatin (Eloxantin™, Sanofi-Synthélabo), dacarbazin (Detimedac™, Medac), cyclophosphamide (Endoxan™, Asta) and carboplatin (Paraplatin™, Bristol-Meyers Squibb), c) cell-cycle inhibitor such as vinorelbine (Navelbine™, Robapharm), vinblastine (Velbe™, Eli Lilly), docetaxel (Taxotere™, Aventis), d) DNA breaker (topoisomerase inhibitor, intercalator, strand breaker) such as doxorubicin HCl (Adriblastin™, Pharmacia-Upjohn), bleomycin (Asta-Medica), irinotecan (Campto™, Aventis), etoposide phosphate (Etopophos™, Bristol-Meyers Squibb), topotecan HCl, (Hycamtin™, GlaxoSmithKline), e) mixtures thereof, f) compounds interfering with the signal transduction pathway, such as caspase activity modifiers, agonists and antagonists of cell death receptors, modifiers of nucleases, phosphatases and kinases such as imatinib mesylate (Gleevec™, Novartis), dexamethasone, phorbol myristate acetate, cyclosporin A, quercetin, tamoxifen (Alexis Corporation, Switzerland).

Apoptosis is determined in a primary screen using a fluorescence plate reader and then in a secondary screen using FACS (fluorescence activated cell scanning). Compounds causing apoptosis without substantial cytotoxic side effects are chosen for further testing and characterization by using a combination of the following well established assays: A) Nuclear staining with Hoechst 33342 dye providing information about nuclear morphology and DNA fragmentation which are hallmarks of apoptosis. B) MTS proliferation assay measuring the metabolic activity of cells. Viable cells are metabolically active whereas cells with compromised respiratory chain show a reduced activity in this test. C) AnnexinV binding assay which reflects the phosphatidylserine content of the outer lipid bilayer of the plasma membrane. This event is considered an early hallmark of apoptosis. D) PI staining for cell cycle distribution which shows any alterations in the distribution among the different phases of the cell cycle. Cell cycle arresting points can be determined. E) Proliferation assay monitoring DNA synthesis by incorporating bromodeoxyuridine (BrdU). Inhibitory effects on growth/proliferation can be directly determined. F) Cystein proteinase dependency, respectively caspase dependency are determined by using specific inhibitors. This provides information about possible involvement of specific proteases in the mechanisms.

On the basis of these studies, a compound of formula (I) according to the invention shows therapeutic efficacy especially against neoplastic diseases and autoimmune diseases. In particular, the compounds of the invention are active against malignancies, e.g. epithelial neoplasms, squamous cell neoplasms, basal cell neoplasms, transitional cell papillomas and carcinomas, adenomas und adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

In particular, a compound of formula (I) according to the invention shows therapeutic efficacy especially against solid neoplastic diseases, e.g. epithelial neoplasms, squamous cell neoplasms, basal cell neoplasms, transitional cell papillomas and carcinomas, adenomas und adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas.

The compounds of the invention are likewise active against autoimmune diseases, e.g. against systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barré syndrome, dermatomyositis/polymyositis, autoimmune hemolytic anemia, thrompocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia greata, primary biliary cirrhosis, autoimmune hepatitis, all forms of glomerulo-nephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopathic and secondary pulmonary fibrosis, inflammatory diseases with a possibility of autoimmune pathogensesis, such as pyoderma gangrensosum, lichen ruber, sarcoidosis (including Löfgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, Henoch-Schoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-VI (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e.g. stem cells).

A compound of formula (I) can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents. A compound of formula (I) can, besides or in addition, be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk. Particularly preferred is the use of compounds of formula (I) in combination with radiotherapy.

Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, an inhibitor of the interaction of an SH2 domain with a phosphorylated protein, an inhibitor of Bcl-2 and modulators of the Bcl-2 family members such as Bax, Bid, Bad, Bim, Nip3 and BH3-only proteins.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

With the groups of preferred compounds of formula (I) mentioned hereinafter, definitions of substituents from the general definitions mentioned hereinbefore may reasonably be used, for example, to replace more general definitions with more specific definitions or especially with definitions characterized as being preferred.

In particular, the invention relates to compounds of formula (I) wherein

R represents aryl or heteroaryl optionally substituted by up to four substituents independently selected from alkyl, cycloalkyl, cycloalkyl-lower alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, cycloalkoxy, halo-lower alkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkylcarbonyloxy, amino, monoalkylamino, dialkylamino, aminocarbonylamino wherein each of the two amino groups is optionally substituted by alkyl, alkenyl, alkinyl or alkoxy-lower alkyl, heterocyclylcarbonylamino wherein heterocyclyl is bound via a nitrogen atom, aminosulfonylamino wherein each of the two amino groups is optionally substituted by alkyl, alkenyl, alkinyl or alkoxy-lower alkyl, heterocyclylsulfonylamino wherein heterocyclyl is bound via a nitrogen atom, lower alkoxycarbonylamino, lower alkylcarbonylamino wherein alkyl is optionally substituted by one or two substituents selected from optionally substituted phenyl, guanidyl, halogen, cyano, alkoxy, optionally substituted phenoxy, alkylmercapto and optionally substituted amino; lower alkenylcarbonylamino wherein alkenyl is optionally substituted by one or two substituents selected from lower alkyl, halo-lower alkyl, optionally substituted phenyl, halogen, cyano, alkoxy and optionally substituted amino; amino-lower alkyl or amino-lower alkylamino, wherein the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heterocyclyl, lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, and nitro; and wherein two adjacent substituents together with the atoms of aryl or heteroaryl may form a 5 or 6 membered carbocyclic or heterocyclic ring;

X represents oxygen; or a group C=Y, wherein Y stands for oxygen, nitrogen substituted by hydroxy or alkoxy;

$R^1$ and $R^2$, independently of each other, represent hydrogen, alkyl, cycloalkyl, cycloalkylalkyl, optionally substituted arylalkyl, optionally substituted heteroarylalkyl, hydroxyalkyl, alkoxyalkyl, hydroxyalkoxyalkyl, alkoxyalkoxyalkyl, cyanoalkyl, optionally substituted alkenyl, optionally substituted alkinyl, or lower alkylcarbonyl wherein lower alkyl is optionally substituted by one or two substitutents selected from aryl, optionally substituted amino, alkoxy and aryloxy, $R^3$, $R^4$, $R^5$ and $R^6$, independently of each other, represent hydrogen, lower alkyl, halo-lower alkyl, cycloalkyl, cycloalkyl-lower alkyl, hydroxy-lower alkyl, lower alkoxy-lower alkyl, lower alkoxy-lower alkoxy-lower alkyl, halo-lower alkoxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, halo-lower alkoxy, cycloalkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, amino, carbamoyl, sulfamoyl, amino-lower alkyl or amino-lower alkylamino, wherein in each case the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heterocyclyl, lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, or nitro, or $R^3$ and $R^4$, $R^4$ and $R^5$, or $R^5$ and $R^6$ together with the atoms of the phenyl ring form a 5 or 6 membered carbocyclic or heterocyclic ring;

and salts thereof.

More particularly the invention relates to compounds of formula (I) wherein

R represents phenyl, naphthyl, thienyl, furyl, thiazolyl, oxadiazolyl, thiadiazolyl, imidazolyl, pyrazolyl, pyridinyl, pyrimidinyl, benzothienyl, benzofuryl, indolyl, benzoisoxazolyl, optionally substituted by up to four substituents independently selected from alkyl, cycloalkyl, cycloalkyl-lower alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, cycloalkoxy, halo-lower alkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkylcarbonyloxy, amino, monoalkylamino, dialkylamino, aminocarbonylamino wherein each of the two amino groups is optionally substituted by alkyl, alkenyl, alkinyl or alkoxy-lower alkyl, heterocyclylcarbonylamino wherein heterocyclyl is bound via a nitrogen atom, aminosulfonylamino wherein each of the two amino groups is optionally substituted by alkyl, alkenyl, alkinyl or alkoxy-lower alkyl, heterocyclylsulfonylamino wherein heterocyclyl is bound via a nitrogen atom, lower alkoxycarbonylamino, lower alkylcarbonylamino wherein alkyl is optionally substituted by one or two substituents selected from optionally substituted phenyl, guanidyl, halogen, cyano, alkoxy, optionally substituted phenoxy, alkylmercapto and optionally substituted amino; lower alkenylcarbonylamino wherein alkenyl is optionally substituted by one or two substituents selected from lower alkyl, halo-lower alkyl, optionally substituted phenyl, halogen, cyano, alkoxy and optionally substituted amino; amino-lower alkyl or amino-lower alkylamino, wherein the nitrogen atom is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heterocyclyl, lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, and nitro;

and wherein two adjacent substituents together with the atoms of aryl or heteroaryl may form a 5 or 6 membered carbocyclic or heterocyclic ring;

X represents oxygen; or a group C=Y, wherein Y stands for oxygen or nitrogen substituted by hydroxy or alkoxy;

$R^1$ and $R^2$, independently of each other, represent hydrogen, lower alkylcarbonyl or optionally substituted phenylcarbonyl;

$R^3$, $R^4$, $R^5$ and $R^6$, independently of each other, represent hydrogen, lower alkyl, halo-lower alkyl, alkoxy, hydroxy-lower alkoxy, lower alkoxy-lower alkoxy, amino, carbamoyl, sulfamoyl, amino-lower alkyl or amino-lower alkylamino, wherein in each case the nitrogen atom is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylaminocarbonyl, or wherein the two substituents on nitrogen form together with the nitrogen heterocyclyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, or nitro, or $R^3$ and $R^4$, $R^4$ and $R^5$, or $R^5$ and $R^6$ together represent methylenedioxy;

and salts thereof.

Preferred are compounds of formula (I) wherein

R represents phenyl, naphthyl, thienyl, furyl, thiazolyl, oxadiazolyl, thiadiazolyl, imidazolyl, pyrazolyl, pyridinyl, pyrimidinyl, benzothienyl, benzofuryl, indolyl, benzoisoxazolyl, optionally substituted by up to four substituents independently selected from alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl, heterocyclyl, heterocylyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, cycloalkoxy, halo-lower alkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkylcarbonyloxy, amino, monoalkylamino, dialkylamino, aminocarbonylamino wherein each of the two amino groups is optionally substituted by alkyl, alkenyl, alkinyl or alkoxy-lower alkyl, heterocyclylcarbonylamino wherein heterocyclyl is bound via a nitrogen atom, aminosulfonylamino wherein each of the two amino groups is optionally substituted by alkyl, alkenyl, alkinyl or alkoxy-lower alkyl, heterocyclylsulfonylamino wherein heterocyclyl is bound via a nitrogen atom, lower alkoxycarbonylamino, lower alkylcarbonylamino wherein alkyl is optionally substituted by one or two substituents selected from optionally substituted phenyl, guanidyl, halogen, cyano, alkoxy, optionally substituted phenoxy, alkylmercapto and optionally substituted amino; lower alkenylcarbonylamino wherein alkenyl is optionally substituted by one or two substituents selected from lower alkyl, halo-lower alkyl, optionally substituted phenyl, halogen, cyano, alkoxy and optionally substituted amino; amino-lower alkyl or amino-lower alkylamino, wherein the nitrogen atom is unsubstituted or substituted by one or two substituents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heterocyclyl, lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, and nitro;

and wherein two adjacent substituents together with the atoms of aryl or heteroaryl may form a 5 or 6 membered carbocyclic or heterocyclic ring;

X represents a group C=Y, wherein Y stands for oxygen or nitrogen substituted by hydroxy or alkoxy;

$R^1$ and $R^2$, independently of each other, represent hydrogen or lower alkylcarbonyl;

$R^3$, $R^4$, $R^5$ and $R^6$, independently of each other, represent hydrogen, lower alkyl, halo-lower alkyl, hydroxy, lower alkoxy, carboxy, lower alkoxycarbonyl, cyano, halogen or nitro;

and salts thereof.

Most preferably, the invention relates to the compounds of the Examples and pharmaceutically acceptable salts, especially to the compounds 4-(1-Phenacyl-1H-benzimidazol-2-yl)-furazan-3-ylamine;
4-(1-Phenacyl-1H-benzimidazol-2-yl)-furazan-3-ylamine oxime;
4-(1-Phenacyl-1H-benzimidazol-2-yl)-furazan-3-ylamine oxime methyl ether;
4-[1-(4-Bromophenacyl)-1H-benzimidazol-2-yl]-furazan-3-ylamine;
4-[1-(4-Bromophenacyl)-1H-benzimidazol-2-yl]-furazan-3-ylamine oxime;
4-[1-(4-Bromophenacyl)-1H-benzimidazol-2-yl]-furazan-3-ylamine oxime methyl ether;
4-[1-(4-Chlorophenacyl)-1H-benzimidazol-2-yl]-furazan-3-ylamine;
4-[1-(4-Chlorophenacyl)-1H-benzimidazol-2-yl]-furazan-3-ylamine oxime;
4-[1-(4-Chlorophenacyl)-1H-benzimidazol-2-yl]-furazan-3-ylamine oxime methyl ether;
4-[1-(4-Methoxyphenacyl)-1H-benzimidazol-2-yl]-furazan-3-ylamine;
4-[1-(4-Methoxyphenacyl)-1H-benzimidazol-2-yl]-furazan-3-ylamine oxime;
4-[1-(3-Methoxyphenacyl)-1H-benzimidazol-2-yl]-furazan-3-ylamine;
4-[1-(3-Methoxyphenacyl)-1H-benzimidazol-2-yl]-furazan-3-ylamine oxime;
4-[1-(3-Methoxyphenacyl)-1H-benzimidazol-2-yl]-furazan-3-ylamine oxime methyl ether;
4-[1-(4-Phenylphenacyl)-1H-benzimidazol-2-yl]-furazan-3-ylamine;
4-[1-(4-Phenylphenacyl)-1H-benzimidazol-2-yl]-furazan-3-ylamine oxime;
4-[1-(4-Phenylphenacyl)-1H-benzimidazol-2-yl]-furazan-3-ylamine oxime methyl ether;
and 4-[1-(2,4-Dichlorophenacyl)-1H-benzimidazol-2-yl]-furazan-3-ylamine;

and to pharmaceutically acceptable salts thereof.

In another embodiment, the invention relates to compounds of formula (I) wherein R represents phenyl, naphthyl, thienyl, furyl, thiazolyl, oxadiazolyl, thiadiazolyl, imidazolyl, pyrazolyl, pyridinyl, pyrimidinyl, benzothienyl, benzofuryl, indolyl, benzoisoxazolyl, optionally substituted by up to four substituents independently selected from alkyl, halo-lower alkyl, hydroxy-lower alkyl, lower alkoxy-lower alkyl, lower alkoxy-lower alkoxy-lower alkyl, halo-lower alkoxy-lower alkyl, acyloxy-lower alkyl, heterocyclyl, heterocyclyl-lower alkyl, optionally substituted phenyl, optionally substituted phenyl-lower alkyl, optionally substituted heteroaryl, optionally substituted heteroaryl-lower alkyl, optionally substituted alkenyl, optionally substituted alkinyl, hydroxy, lower alkoxy, optionally substituted alkenyloxy, optionally substituted alkinyloxy, cycloalkoxy, halo-lower alkoxy, cycloalkyl-lower alkoxy, hydroxy-lower alkoxy, lower alkoxy-lower alkoxy, heterocyclyloxy, heterocyclyl-lower alkoxy, optionally substituted phenyloxy, optionally substituted phenyl-lower alkoxy, optionally substituted heteroaryloxy, optionally substituted heteroaryl-lower alkoxy, sulfamoyloxy, carbamoyloxy, lower alkylcarbonyloxy, amino, monoalkylamino, dialkylamino, aminocarbonylamino wherein each of the two amino groups is optionally substituted by alkyl, alkenyl, alkinyl or alkoxy-lower alkyl, heterocyclylcarbonylamino wherein heterocyclyl is bound via a nitrogen atom, aminosulfonylamino wherein each of the two amino groups is optionally substituted by alkyl, alkenyl, alkinyl or alkoxy-lower alkyl, heterocyclylsulfonylamino wherein heterocyclyl is bound via a nitrogen atom, lower alkoxycarbonylamino, lower alkylcarbonylamino wherein alkyl is optionally substituted by one or two substituents selected from optionally substituted phenyl, guanidyl, halogen, cyano, alkoxy, optionally substituted phenoxy, alkylmercapto and optionally substituted amino; lower alkenylcarbonylamino wherein alkenyl is optionally substituted by one or two substituents selected from lower alkyl, halo-lower alkyl, optionally substituted phenyl, halogen, cyano, alkoxy and optionally substituted amino; amino-lower alkyl or amino-lower alkylamino, wherein the nitrogen atom is unsubstituted or substituted by one or two substitutents selected from lower alkyl, cycloalkyl, cycloalkyl-lower alkyl, hydroxy-lower alkyl, lower alkoxy-lower alkyl, optionally substituted phenyl, optionally substituted phenyl-lower alkyl, optionally substituted heteroaryl, optionally substituted heteroaryl-lower alkyl and lower alkylcarbonyl, or wherein the two substituents on nitrogen form together with the nitrogen heterocyclyl, lower alkylcarbonyl, cycloalkylcarbonyl, optionally substituted phenylcarbonyl, optionally substituted heteroarylcarbonyl, heterocyclylcarbonyl, carboxy, lower alkoxycarbonyl, hydroxy-lower alkoxycarbonyl, lower alkoxy-lower alkoxycarbonyl, optionally substituted phenyl-lower alkoxycarbonyl, cyano, lower alkylmercapto, optionally substituted phenylmercapto, lower alkylsulfinyl, halo-lower alkylsulfinyl, optionally substituted phenylsulfinyl, lower alkylsulfonyl, halo-lower alkylsulfonyl, optionally substituted phenylsulfonyl, aralkylsulfonyl, halogen, and nitro;

and wherein two adjacent substituents together with the atoms of aryl or heteroaryl may form a 5 or 6 membered carbocyclic or heterocyclic ring;

X represents a group C=Y, wherein Y stands for oxygen or nitrogen substituted by hydroxy or alkoxy;

$R^1$ represents cyanoalkyl;

$R^2$ represents hydrogen;

$R^3$, $R^4$, $R^5$ and $R^6$, independently of each other, represent hydrogen, lower alkyl, halo-lower alkyl, hydroxy, lower alkoxy, carboxy, lower alkoxycarbonyl, cyano, halogen or nitro;

and salts thereof.

Alternatively, the invention relates to compounds of formula (I) wherein R, X and $R^2$ to $R^6$ are as defined in the preceding paragraphs and $R^1$ represents hydroxyalkyl, and salts thereof.

In yet another embodiment, the invention relates to compounds of formula (I) wherein R represents phenyl, thienyl, pyridinyl or pyridazinyl, optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, formyl, carboxy, lower alkoxycarbonyl, cyano, halogen, and nitro;

and wherein two adjacent substituents are methylenedioxy;

X represents oxygen; a group C=Y, wherein Y stands for oxygen or nitrogen substituted by hydroxy or alkoxy; or a group —CO—CH=CH— wherein the C=C bond is connected to R;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and salts thereof.

Preferred are compounds of formula (I) wherein

R represents phenyl, thienyl, pyridinyl or pyridazinyl, wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, formyl, carboxy, lower alkoxycarbonyl, cyano, halogen, and nitro; and wherein two adjacent substituents are methylenedioxy;

and wherein pyridinyl or pyridazinyl are optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable salts thereof.

More preferred are compounds of formula (I) wherein

R represents phenyl, thienyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable salts thereof.

Particularly preferred are compounds of formula (I) wherein

R represents phenyl, thienyl, pyridinyl or pyridazinyl, wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, formyl, carboxy, lower alkoxycarbonyl, cyano, halogen, and nitro; and wherein two adjacent substituents are methylenedioxy;

and wherein pyridinyl or pyridazinyl are optionally substituted by lower alkoxy, amino or halogen;

X represents a group C=Y, wherein Y stands for oxygen or nitrogen substituted by hydroxy or lower alkoxy;

$R^1$ represents cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable salts thereof.

Highly preferred are compounds of formula (I) wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;

X represents oxygen;

R[1] represents hydrogen, lower alkylcarbonyl, hydroxy-lower alkyl or cyano-lower alkyl;

R[2], R[3] and R[6] represent hydrogen;

R[4] and R[5], independently of each other, represent hydrogen, lower alkyl or lower alkoxy;

or R[4] and R[5] together represent methylenedioxy;

and pharmaceutically acceptable salts thereof.

Likewise preferred are compounds of formula (I) wherein R and R[1] to R[6] are defined as in the preceding paragraphs, and X represents nitrogen substituted by alkoxy, and pharmaceutically acceptable salts thereof.

Other preferred compounds that come into consideration are compounds of formula (I)

wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;

X represents oxygen;

R[1] represents cyano-lower alkyl;

R[2], R[3], R[4], R[5] and R[6] represent hydrogen;

and pharmaceutically acceptable salts thereof.

More preferred are compounds of formula (I) wherein

R represents phenyl or pyridinyl wherein phenyl is optionally substituted by one or two substituents independently selected from alkyl, lower alkoxy-lower alkyl, acyloxy-lower alkyl, hydroxy, lower alkoxy, hydroxy-lower alkoxy, lower alkoxy-lower alkoxy, amino, monoalkylamino, dialkylamino, lower alkoxycarbonylamino, lower alkylcarbonylamino, substituted amino wherein the two substituents on nitrogen form together with the nitrogen heterocyclyl, halogen, and nitro;

and wherein two adjacent substituents are methylenedioxy;

and wherein pyridinyl is optionally substituted by lower alkoxy, amino or halogen;

X represents oxygen;

R[1] represents cyano-lower alkyl;

R[2], R[3], R[4], R[5] and R[6] represent hydrogen;

and pharmaceutically acceptable salts thereof.

Particularly preferred are compounds of formula (I) according to claim 8 wherein R represents phenyl or pyridinyl wherein phenyl is optionally substituted by one or two substituents independently selected from alkyl, lower alkoxy-lower alkyl, acyloxy-lower alkyl, hydroxy, lower alkoxy, hydroxy-lower alkoxy, lower alkoxy-lower alkoxy, amino, monoalkylamino, dialkylamino, lower alkoxycarbonylamino, lower alkylcarbonylamino, substituted amino wherein the two substituents on nitrogen form together with the nitrogen heterocyclyl, halogen, and nitro;

and wherein two adjacent substituents are methylenedioxy;

and wherein pyridinyl is optionally substituted by lower alkoxy, amino or halogen;

X represents nitrogen substituted by alkoxy;

R[1] represents cyano-lower alkyl;

R[2], R[3], R[4], R[5] and R[6] represent hydrogen;

and pharmaceutically acceptable salts thereof.

Other preferred compounds of formula (I) are those wherein

R represents phenyl optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

X represents a group —CO—CH=CH— wherein the C=C bond is connected to R;

R[1] represents cyano-lower alkyl;

R[2], R[3], R[4], R[5] and R[6] represent hydrogen;

and pharmaceutically acceptable salts thereof.

Most preferred are compounds selected from the group consisting of

4-[1-(4-Chlorophenacyl)-1H-benzimidazol-2-yl]-furazan-3-yl-N-(2-cyanoethyl)-amine;

4-[1-(3-Methoxy-4-methoxymethoxy-phenacyl)-1H-benzimidazol-2-yl]-furazan-3-ylamine;

4-[1-(4-Bromophenacyl)-1H-benzimidazol-2-yl]-furazan-3-yl-N-(2-cyanoethyl)-amine;

4-[1-(4-Aminophenacyl)-1H-benzimidazol-2-yl]-furazan-3-yl-N-(2-cyanoethyl)-amine;

4-[1-(4-Methoxyphenacyl)-1H-benzimidazol-2-yl]-furazan-3-yl-N-(2-cyanoethyl)-amine;

4-[1-(3,4-Dimethylphenacyl)-1H-benzimidazol-2-yl]-furazan-3-yl-N-(2-cyanoethyl)-amine;

4-[1-(4-Ethylphenacyl)-1H-benzimidazol-2-yl]-furazan-3-yl-N-(2-cyanoethyl)-amine;

4-[1-(6-Chloro-3-pyridyl)-1H-benzimidazol-2-yl]-furazan-3-ylamine;

4-[1-(6-Amino-3-pyridyl)-1H-benzimidazol-2-yl]-furazan-3-yl-N-(2-cyanoethyl)-amine; and 4-[1-(6-Amino-3-pyridyl)-1H-benzimidazol-2-yl]-furazan-3-ylamine;

and pharmaceutically acceptable salts thereof.

Especially, the invention relates to compounds as described hereinbefore for use as medicaments.

The invention also relates to the use of a compound of formula (I), a prodrug or a pharmaceutically acceptable salt of such a compound for the preparation of a pharmaceutical composition for the treatment of a neoplastic disease, autoimmune disease, transplantation related pathology and/or degenerative disease, in particular for the treatment of a solid neoplastic disease.

Furthermore, the invention provides a method for the treatment of a neoplastic disease, autoimmune disease, transplantation related pathology and/or degenerative disease, in particular of a solid neoplastic disease, which comprises administering a compound of formula (I), a prodrug or a pharmaceutically acceptable salt thereof, wherein the radicals and symbols have the meanings as defined above, in a quantity effective against said disease, to a warm-blooded animal requiring such treatment.

Method of Preparation

A compound of the invention may be prepared by processes that, though not applied hitherto for the new compounds of the present invention, are known per se, in particular A) a process, wherein a compound of formula (II)

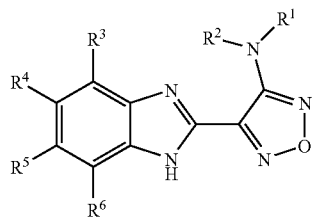

(II)

wherein $R^1$, $R^2$, $R^3$, $R^4$, $R^5$ and $R^6$ are defined as for formula (I), or a derivative thereof with functional groups in protected form and/or a salt thereof, is alkylated with an alkylating agent of formula (III)

(III)

wherein R is as defined for formula (I), X is CO or —CO—CH=CH— and Z is a nucleophilic leaving group;

or

B) a process, wherein a compound of formula (II) wherein $R^1$, $R^2$, $R^3$, $R^4$, $R^5$ and $R^6$ are defined as for formula (I), or a derivative thereof with functional groups in protected form and/or a salt thereof, is alkylated with a mixture of a dihalomethane type compound of formula $Z^1$-$CH_2$-$Z^2$ (IV), wherein $Z^1$ and $Z^2$ are leaving groups, and a compound of formula R—XH (V), wherein R is as defined for formula (I) and X is oxygen;

any protecting groups in a protected derivative of a compound of the formula (I) are removed;

and, if so desired, an obtainable compound of formula (I) is converted into another compound of formula (I), a free compound of formula (I) is converted into a salt, an obtainable salt of a compound of formula (I) is converted into the free compound or another salt, and/or a mixture of isomeric compounds of formula (I) is separated into the individual isomers.

Suitable nucleophilic leaving groups Z in an alkylating agent of formula (III) are for example halides, e.g. chloride, bromide or iodide, or sulfonates, e.g. aromatic sulfonic acid esters such as benzenesulfonates, p-toluenesulfonates or p-nitrobenzenesulfonates, or also methanesulfonate or trifluormethanesulfonate. Also other customary leaving groups are considered, e.g. ammonium salts, azides, diazonium salts, di(p-toluenesulfonyl)-amines, nitrates, oxonium salts, sulfonium salts, or phosphonium salts. Suitable nucleophilic leaving groups $Z^1$ and $Z^2$ in a dihalomethane type compound formula (IV) are those mentioned above, in particular chlorine, bromine and iodine.

Alkylation of a compound of formula (II) with an alkylating agent of formula (III) is performed in a manner known per se, usually in the presence of a suitable polar or dipolar aprotic solvent, with cooling or heating, for example in a temperature range from approximately −30° C. to approximately +150° C., especially approximately around 0° C. to room temperature. Optionally a suitable base is added, in particularly a tertiary amine base such as triethylamine or diisopropylethylamine, or an inorganic basic salt, e.g. potassium or sodium carbonate.

Mixed alkylation of a compound of formula (II) and of a compound of formula (V) with a dihalomethane type compound of formula (IV) is performed in the presence of a suitable polar or dipolar aprotic solvent, with cooling or heating, for example in a temperature range from approximately −30° C. to approximately +150° C., especially approximately around 0° C. to room temperature. Suitable bases used in this reaction are for example potassium and sodium carbonate.

If one or more other functional groups, for example carboxy, hydroxy or amino, are or need to be protected in a compound of formula (II), (III) or (V), because they should not take part in the reaction, these are such protecting groups as are usually applied in the synthesis of amides, in particular peptide compounds, cephalosporins, penicillins, nucleic acid derivatives and sugars.

The protecting-groups may already be present in precursors and should protect the functional groups concerned against unwanted secondary reactions, such as alkylations, acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/1, Georg Thieme Verlag, Stuttgart 1974, and in T. W. Greene, "Protective Groups in Organic Synthesis", Wiley, New York.

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

In the conversion of an obtainable compound of formula (I) into another compound of formula (I), X with the meaning C=Y wherein Y is oxygen may, for example, be reacted with an optionally O-substituted hydroxylamine to give the corresponding oxime or oxime ether of formula (I) wherein X is C=Y and Y is nitrogen substituted by hydroxy or alkoxy.

An obtainable compound of formula (I), wherein $R^1$ and/or $R^2$ is hydrogen, may be alkylated or acylated with a compound of formula $R^1$-Z or $R^2$-Z, respectively, wherein Z is a nucleophilic leaving group as described above, to give a compound of formula (I), wherein $R^1$ and/or $R^2$ is different from hydrogen. Preferred acylation conditions include the use of acid anhydrides and acid chlorides at elevated temperatures, typically in a range from approximately +30° C. to approximately +150° C. An acidic or basic catalyst may be employed if desired. A compound of formula (I) wherein $R^1$ and/or $R^2$ is alkyl may be obtained by alkylation of the parent compound of formula (I). Typical reaction conditions allowing this transformation include the combination of a strong base, such as a metal hydride or a metal alcoholate and a compound of formula $R^1$-Z or $R^2$-Z.

Further amino groups present in an aryl or heteroaryl group R or in one of the substitutents $R^3$, $R^4$, $R^5$ or $R^6$ may be transformed to other nitrogen containing substituents under conditions known in the art. For example, alkylation at nitrogen may be performed with an aldehyde under reducing conditions. For acylation the corresponding acyl chloride (Z=Cl) is preferred. Alternatively, an acid anhydride may be used, or acylation may be accomplished with the free acid (Z=OH) under conditions used for amide formation known per se in peptide chemistry, e.g. with activating agents for the carboxy group, such as 1-hydroxybenzotriazole, optionally in the presence of suitable catalysts or co-reagents.

Compounds of formula (I) wherein X=NOH may be alkylated allowing access to the corresponding oxime ethers. The reaction conditions leading to this transformation include combinations of weak bases and alkylating agents. Typical bases include metal carbonates or bicarbonates.

Reduction of a nitro group in an nitro-substituted aryl or heteroaryl group R or in one of the substituents $R^3$, $R^4$, $R^5$ or $R^6$ to give the corresponding amino group is done, e.g., with iron powder in alcohol or with other reducing agents.

A carboxy group in a carboxy-substituted aryl or heteroaryl group R or in one of the substituents $R^3$, $R^4$, $R^5$ or $R^6$ may be amidated under conditions used for amide formation known per se in peptide chemistry, e.g. with the corresponding amine and an activating agent for the carboxy group, such as 1-hydroxybenzotriazole, optionally in the presence of suitable catalysts or co-reagents.

A bromo or iodo substitutent in an aryl or heteroaryl group R or in one of the substituents $R^3$, $R^4$, $R^5$ or Re may be replaced by phenyl or a phenyl derivative by reaction with a suitable phenylboronic acid in a Suzuki reaction, preferably in a dipolar aprotic solvent such as dimethyl formamide, or in a polar ether, e.g. tetrahydrofuran or dimethoxyethane, in the presence of a soluble palladium(0) or related metal catalyst, for example tetrakis-(triphenylphosphine) palladium.

Salts of a compound of formula (I) with a salt-forming group may be prepared in a manner known per se. Acid addition salts of compounds of formula (I) may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

It should be emphasized that reactions analogous to the conversions mentioned in this chapter may also take place at the level of appropriate intermediates.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the $H^+$ form, depending on the type of reaction and/or reactants at reduced, normal, or elevated temperature, for example in the range from −100° C. to about 190° C., preferably from about −80° C. to about 150° C., for example at −80 to +60° C., at −20 to +40° C., at room temperature, or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and further processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula (I) is prepared according to or in analogy to the processes and process steps defined in the Examples.

The compounds of formula (I), including their salts, are also obtainable in the form of hydrates, or their crystals can include for example the solvent used for crystallization, i.e. be present as solvates.

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of formula (II), (III), (IV) and (V) are known, commercially available, or can be synthesized in analogy to or according to methods that are known in the art.

Pharmaceutical Preparations, Methods, and Uses

The present invention relates also to pharmaceutical compositions that comprise a compound of formula (I) as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula (I), a tautomer, a prodrug or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, in particular in a method of treating neoplastic disease, autoimmune disease, transplantation related pathology and/or degenerative disease, especially those mentioned hereinabove.

The invention relates also to processes and to the use of compounds of formula (I) thereof for the preparation of pharmaceutical preparations which comprise compounds of formula (I) as active component (active ingredient).

A pharmaceutical composition for the prophylactic or especially therapeutic management of a neoplastic disease, autoimmune disease, transplantation related pathology and/or degenerative disease, of a warm-blooded animal, especially a human or a commercially useful mammal requiring such treatment, comprising a novel compound of formula (I) as active ingredient in a quantity that is prophylactically or especially therapeutically active against the said diseases, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetyl-cellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a neoplastic disease, autoimmune disease, transplantation related pathology and/or degenerative disease, which comprises administering a compound of formula (I) or a pharmaceutically acceptable salt thereof, wherein the radicals and symbols have the meanings as defined above for formula (I), in a quantity effective against said disease, to a warm-blooded animal requiring such treatment. The compounds of formula (I) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The present invention relates especially also to the use of a compound of formula (I), or a pharmaceutically acceptable salt thereof, especially a compound of formula (I) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, in particular a neoplastic disease, autoimmune disease, transplantation related pathology and/or degenerative disease.

The preferred dose quantity, composition, and preparation of pharmaceutical formulations (medicines) which are to be used in each case are described above.

The following Examples serve to illustrate the invention without limiting the invention in its scope.

EXAMPLES

Abbreviations: DMSO dimethyl=sulfoxide; THF=tetrahydrofuran, DMAP=N,N-dimethylaminopyridine, DMF=N,N-dimethylformamide, DIPEA=N,N-diisopropyl-N-ethylamine.

Example 1

4-(1-Phenacyl-1H-benzimidazol-2-yl)-furazan-3-ylamine

Phenacylbromid (0.1 g, 0.49 mmol) is added to an efficiently stirred suspension of 4-(1H-benzimidazol-2-yl)-furazan-3-ylamine (0.1 g, 0.4 mmol) [A. V. Sergievskii, O. A. Krasnoshek, S. F. Mel'nikova, I. V. Tselinskii, Russian Journal of Organic Chemistry, 2002, 38, 915-917] and potassium carbonate (0.172 g, 1.24 mmol) in dry DMF (5 ml) at room temperature. After 4 hours the reaction mixture is diluted with ethyl acetate and the organic phase is washed repeatedly with brine. Drying of the solvent, filtering and evaporation of the solvent under reduced pressure gives the title compound in crude form. The title compound is obtained in pure form by chromatography over silicagel, m.p. 202-204° C.

Example 2

4-[1-(4-Bromophenacyl)-1H-benzimidazol-2-yl]-furazan-3-ylamine oxime

A mixture of 4-[1-(4-bromophenacyl)-1H-benzimidazol-2-yl]-furazan-3-ylamine (0.083 g, 0.21 mmol, prepared according to Example 1), sodium bicarbonate (0.021 g, 0.25 mmol) and hydroxylamine hydrochloride (0.014 g, 0.21 mmol) in ethanol (5 ml) is refluxed for 20 hours. Partitioning of the reaction mixture between ethyl acetate and water, separation of the organic phase followed by drying and evaporation of the solvent gives the crude product. Purification by chromatography on silicagel yields the title compound as an E/Z-mixture, m.p. 198-201° C.

Example 3

Methyl-{4-[1-(4-chlorophenacyl)-1H-benzimidazol-2-yl]-furazan-3-yl}-amine

A suspension of 4-[1-(4-chlorophenacyl)-1H-benzimidazol-2-yl]-furazan-3-ylamine (0.10 g, 0.282 mmol, prepared according to Example 1), potassium carbonate (0.233 g, 1.69 mmol) and dimethylsulfate (0.142 g, 1.12 mmol) in acetone (5 ml) is stirred at room temperature for 16 hours. Filtration of the solids, concentration of the filtrate under reduced pressure and chromatography of the residue on silicagel using hexane-ethyl acetate as eluent gives the title compound as a colorless solid, m.p. 210-214° C.

Example 4

Dimethyl-{4-[1-(4-chlorophenacyl)-1H-benzimidazol-2-yl]-furazan-3-yl}-amine

A suspension of 4-[1-4-chlorophenacyl)-1H-benzimidazol-2-yl]-furazan-3-ylamine (0.10 g, 0.282 mmol), potassium carbonate (0.60 g, 4.22 mmol) and dimethylsulfate (0.50 g, 2.82 mmol) in DMF (5 ml) is stirred at 60° C. for 6 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as a yellowish solid, m.p. 120-123° C.

Example 5

N-{4-[1-(4-Chlorophenacyl)-1H-benzimidazol-2-yl]-furazan-3-yl}-acetamide

A solution of 4-[1-(4-chlorophenacyl)-1H-benzimidazol-2-yl]-furazan-3-ylamine (0.05 g, 0.143 mmol), pyridine (0.022 g, 0.282 mmol), acetyl chloride (0.013 g, 0.169 mmol) and a catalytic amount of DMAP in DMF (5 ml) is stirred at 80° C. for 16 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as a yellowish solid, m.p. 202-205° C.

Example 6

4-[1-(4-Chlorophenacyl)-1H-benzimidazol-2-yl]-furazan-3-yl-N-(2-cyanoethyl)-amine A suspension of 4-(1H-benzimidazol-2-yl)-furazan-3-yl-N-(2-cyanoethyl)-amine (0.10 g, 0.39 mmol), potassium carbonate (0.08 g, 0.58 mmol) and 4-chlorophenacyl bromide (0.11 g, 0.47 mmol) in DMF (5 ml) is stirred at room temperature for 16 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as a yellowish solid, m.p. 191-192° C.

Example 6a

4-(1H-Benzimidazol-2-yl)-furazan-3-yl-N-(2-cyanoethyl)-amine

To a solution of 4-(1H-benzimidazol-2-yl)-furazan-3-ylamine (0.10 g, 0.497 mmol) in pyridine (5 ml) sodium in methanol (0.02 g, 0.86 mmol in 1 ml) and acrylonitrile (0.03 g, 0.39 mmol) are added sequentially at 0° C. The mixture is stirred over night. Evaporation of the solvent under reduced pressure and partitioning of the resulting residue between water and ethyl acetate followed by drying of the organic solution over sodium sulphate gives the title compound in pure form. $^1$H-NMR (400 MHz, d$^6$-DMSO): 13.7 (s, 1H); 7.82 (d, 1H); 7.60 (d, 1H); 7.36 (m, 2H); 7.20 (t, 1H); 3.67 (q, 2H); 2.94 (t, 2H).

Example 7

4-(1-Phenoxymethyl-1H-benzimidazol-2-yl)-furazan-3-ylamine

To a solution of 4-(1H-benzimidazol-2-yl)-furazan-3-ylamine (0.10 g, 0.497 mmol) is added potassium carbonate (0.172 g, 1.24 mmol) and iodomethoxy benzene (0.128 g, 0.546 mmol). The mixture is stirred over night. Evaporation of the solvent under reduced pressure and partitioning of the resulting residue between water and ethyl acetate followed by drying of the organic solution over sodium sulphate and chromatography of the residue gives the title compound as a colorless solid, m.p. 171-173° C.

Example 8

4-[1-(4-Fluorophenoxymethyl)-1H-benzimidazol-2-yl]-furazan-3-ylamine

To a solution of 4-(1H-benzimidazol-2-yl)-furazan-3-ylamine (0.10 g, 0.497 mmol) is added potassium carbonate (0.172 g, 1.24 mmol) followed by 4-fluorophenol (0.0557 g, 0.497 mmol) and diiodomethane (0.133 g, 0.497 mmol). The mixture is stirred over night. Evaporation of the solvent under reduced pressure and partitioning of the resulting residue between water and ethyl acetate followed by drying of the organic solution over sodium sulphate and chromatography of the residue gives the title compound as a colorless solid, m.p. 155-158° C.

Example 9

4-[1-(4-Chlorophenacyl)-1H-benzimidazol-2-yl]-furazan-3-yl-N-(2-methoxycarbonylethyl)-amine A suspension of 4-(1H-benzimidazol-2-yl)-furazan-3-yl-N-(2-methoxycarbonylethyl)-amine (0.052 g, 0.181 mmol), potassium carbonate (0.062 g, 0.452 mmol) and 4-chlorophenacyl bromide (0.047 g, 0.199 mmol) in DMF (5 ml) is stirred at room temperature for 16 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as hygroscopic solid of undefined melting point. $^1$H-NMR (400 MHz, d$^6$-DMSO): 8.14 (d, 2H); 7.87 (m, 2H); 7.41 (m, 2H); 7.32 (d, 2H); 7.29 (t, 1H); 6.37 (s, 2H); 3.63 (m, 2H); 3.61 (s, 3H); 2.76 (t, 2H).

Example 9a

4-[1-(1H-Benzimidazol-2-yl]-furazan-3-yl-N-(2-methoxycarbonylethyl)-amine

A solution of 4-(1H-benzimidazol-2-yl)-furazan-3-yl-N-(2-cyanoethyl)-amine (0.05 g, Example 6a) in methanol saturated with hydrochloric acid (5 ml) is heated at reflux for 40 minutes. After addition of a drop of water refluxing is continued for 2 hours. The mixture is neutralized using sodium bicarbonate and then extracted repeatedly using ethyl acetate. The combined organic extracts are dried and evaporated to dryness under reduced pressure. Trituration with hexane and filtering yields the title compound in pure form. $^1$H-NMR (400 MHz, d$^6$-DMSO): 13.8 (s, 1H); 7.80 (m, 1H); 7.59 (m, 1H); 7.32 (m, 2H); 703 (m, 1H); 3.63 (m, 2H); 3.61 (s, 3H); 2.76 (t, 2H).

Example 10

4-[1-(3,4-Dimethylphenoxymethyl)-1H-benzimidazol-2-yl]-furazan-3-yl-N-(2-cyanoethyl)-amine A suspension of 4-(1H-benzimidazol-2-yl)-furazan-3-yl-N-(2-cyanoethyl)-amine (0.15 g, 0.59 mmol, Example 6a), potassium carbonate (0.325 g, 2.36 mmol), diiodomethane (0.16 g, 0.59 mmol) and 3,4-dimethylphenol (0.072 g, 0.59 mmol) in DMF (5 ml) is stirred at room temperature for 16 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as a yellowish solid, m.p. 132-135° C.

Example 11

4-[1-(4-Chlorophenacyl)-1H-benzimidazol-2-yl]-furazan-3-yl-N-(3-hydroxypropyl)-amine A suspension of 4-(1H-benzimidazol-2-yl)-furazan-3-yl-N-(3-hydroxypropyl)-amine (0.70 g, 0.27 mmol), potassium carbonate (0.472 g, 3.42 mmol) and 4-chlorophenacyl bromide (0.069 g, 0.29 mmol) in DMF (5 ml) is stirred at room temperature for 16 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as a yellowish solid, m.p. 166-169° C.

Example 11a

4-(1H-Benzimidazol-2-yl)-furazan-3-yl-N-(3-hydroxypropyl)-amine

A solution of 4-(1H-benzimidazol-2-yl)-furazan-3-yl-N-(2-cyanoethyl)-amine (0.272 g, 0.947 mmol, Example 6a) in THF (5 ml) is added dropwise at 0° C. to an efficiently stirred suspension of LiAlH$_4$ (0.054 g, 1.42 mmol) in THF (5 ml). After stirring for 16 hours at room temperature the mixture is quenched by careful addition of aqueous saturated solution of sodium sulphate. The suspension is filtered and the filtrate evaporated to dryness. Crystallization by addition of hexane yields the title compound in pure form. $^1$H-NMR (400 MHz, d$^6$-DMSO): 13.6 (s, 1H); 7.66 (m, 2H); 7.31 (m, 2H); 6.92 (t, 1H); 4.61 (m, 1H); 3.51 (m, 2H); 3.39 (m, 2H); 1.81 (m, 2H).

Example 12

E-1-[2-(4-Aminofurazan-3-yl)-benzimidazol-1-yl]-4-phenyl-but-3-en-2-one

A suspension of 4-(1H-benzimidazol-2-yl)-furazan-3-ylamine (0.275 g, 1.37 mmol), potassium carbonate (0.472 g, 3.42 mmol) and 1-chloro-4-phenyl-but-3-en-2-one (0.297 g, 1.64 mmol) in DMF (5 ml) is stirred at room temperature for 16 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as a yellowish solid, m.p. 176-180° C.

Example 12a

1-Chloro-4-phenyl-but-3-en-2-one

A mixture of 1-chloro-3-(triphenylphosphanylidene)-propane-2-one (2.8 g, 7.9 mmol) and freshly distilled benzaldehyde (0.7 g, 6.6 mmol) in toluene (10 ml) is heated at reflux for 20 hours. Evaporation to dryness yields a mixture containing the title compound that is used in the subsequent step without purification.

Example 12b

1-Chloro-3-(triphenylphosohanylidene)-propane-2-one

A mixture of triphenylphosphine (10.0 g, 38.1 mmol) and 1,3-dichloroacetone (4.84 g, 38.1 mmol) in THF (20 ml) is heated at reflux for 4 hours. On cooling the resulting precipitate is filtered, washed with THF and dried. To the efficiently stirred precipitate in methanol (20 ml) a 20% aqueous solution of sodium carbonate (2.02 g, 19 mmol) is added followed by additional water. The resulting product is filtered and dried to yield the pure product. $^1$H-NMR (400 MHz, d$^6$-DMSO): 7.61 (m, 15H); 4.07 (2s, 0.5H each); 3.98 (s, 2H).

Example 13

4-[1-(4-Aminophenacyl)-1H-benzimidazol-2-yl]-furazan-3-yl-N-(2-carboxyethyl)-amine A solution of 4-[1-(4-acetaminophenacyl)-1H-benzimidazol-2-yl]-furazan-3-yl-N-(2-cyanoethyl)-amine (0.061 g) in aqueous hydrochloric acid (5 ml, HCl conc.) is heated at reflux for two hours. The mixture is diluted with water and neutralized by addition of sodium bicarbonate. Extraction with ethyl acetate, drying over sodium sulphate, filtering and evaporation of the resulting filtrate to dryness gives the title compound in pure form, m.p. 174-177° C. $^1$H-NMR (400 MHz, d$^6$-DMSO): 12.40 (s, 1H); 7.84 (m, 4H); 7.38 (m, 3H); 6.65 (m, 2H); 6.28 (S, 2H); 6.17 (s, 2H); 3.57 (m, 2H); 2.66 (t, 2H).

Example 14

4-[1-(3-Amino-4-chlorophenacyl)-1H-benzimidazol-2-yl]-furazan-3-ylamine

To a stirred solution of 4-[1-(4-chloro-3-nitrophenacyl)-1H-benzimidazol-2-yl]-furazan-3-ylamine (0.07 g, 0.175 mmol) in ethanol (6 ml) and water (1 ml) is added two drops of concentrated hydrochloric acid and iron powder (0.1 g, 17.5 mmol). The reaction mixture is heated at 80° C. for 8 hours. Filtration and evaporation at reduced pressure gives the crude product. Purification by extraction with ethyl acetate and chromatography on silicagel yields the title compound as colorless solid, m.p. 228-230° C.

Example 14a

4-[1-(4-Chloro-3-nitrophenacyl)-1H-benzimidazol-2-yl]-furazan-3-ylamine

A suspension of 4-(1H-benzimidazol-2-yl)-furazan-3-ylamine (0.228 g, 1.14 mmol), potassium carbonate (0.40 g, 2.85 mmol) and 4-chloro-3-nitrophenacyl bromide (0.35 g, 1.25 mmol) in DMF (5 ml) is stirred at room temperature for 16 hours. The reaction mixture is diluted with ethyl acetate, washed with water and dried over sodium sulphate. Filtration of the sodium sulphate, concentration of the filtrate under reduced pressure and chromatography of the residue on silicagel using hexane-ethyl acetate as eluent gives the title compound as a solid, m.p. 198-200° C. (This compound is also listed as Example 66 in Table 1.)

Example 15

4-[1-(3-Methoxy-4-methoxymethoxy-phenacyl)-1H-benzimidazol-2-yl]-furazan-3-ylamine A mixture of 4-[1-(3-methoxy-4-hydroxyphenacyl)-1H-benzimidazol-2-yl]-furazan-3-ylamine (0.10 g, 0.27 mmol), DIPEA and methoxymethyl chloride in dry DMF is stirred at room temperature for 14 hours. The reaction mixture is diluted with ethyl acetate, washed with water and dried over sodium sulphate. Filtration of the sodium sulphate and concentration of the filtrate under reduced pressure gives the title compound as colorless, pure solid, m.p. 190° C.

Example 15a

4-[1-(3-Methoxy-4-hydroxyphenacyl)-1H-benzimidazol-2-yl]-furazan-3-yl-amine

To a solution of 4-[1-(3-methoxy-4-benzyloxyphenacyl)-1H-benzimidazol-2-yl]-furazan-3-ylamine (1.00 g) in THF (20 ml) is added palladium on carbon (10%, 0.2 g). The mixture is stirred under a hydrogen atmosphere for 1 hour. The catalyst is filtered and the filtrate is evaporated to dryness to give the title compound in pure form, m.p. 265° C. (This compound is also listed as Example 74 in Table 1.)

The following compounds are prepared in analogy to Examples 1-15:

TABLE 1

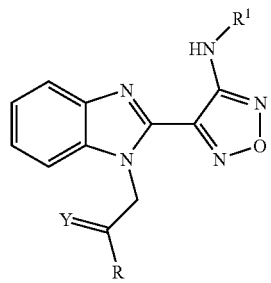

| Ex | R | Y | R¹ | Salt | Comment | m.p. |
|---|---|---|---|---|---|---|
| 16 | 4-Cl-C₆H₄ | O | H | — | — | 198–200° C. |
| 17 | C₆H₅ | NOH | H | — | E/Z | 210° C. |
| 18 | C₆H₅ | NOMe | H | — | E/Z | 156–158° C. |
| 19 | 4-MeO-C₆H₄ | O | H | — | — | 160–162° C. |
| 20 | 4-MeO-C₆H₄ | NOH | H | — | E/Z | 176–178° C. |
| 21 | 4-Cl-C₆H₄ | NOH | H | — | E/Z | 204–206° C. |
| 22 | 4-Cl-C₆H₄ | NOMe | H | — | E/Z | 206–208° C. |
| 23 | 3-MeO-C₆H₄ | O | H | — | — | 181–184° C. |
| 24 | 3-MeO-C₆H₄ | NOH | H | — | E/Z | 189–192° C. |

TABLE 1-continued
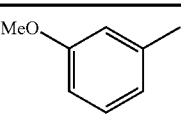
| Ex | R | Y | R¹ | Salt | Comment | m.p. |
|----|---|---|----|----|---------|------|
| 25 | 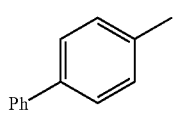 MeO- (meta) | NOMe | H | — | E/Z | 160° C. |
| 26 | 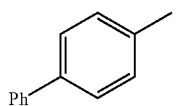 Ph- (para) | O | H | — | — | 226–228° C. |
| 27 | 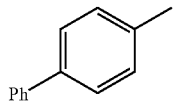 Ph- (para) | NOH | H | — | E/Z | 196–198° C. |
| 28 | 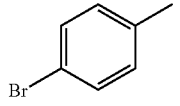 Ph- (para) | NOMe | H | — | E/Z | 164–166° C. |
| 29 | 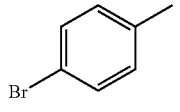 Br- (para) | O | H | — | — | 212–214° C. |
| 30 | 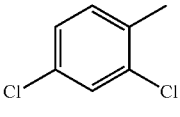 Br- (para) | NOMe | H | — | E/Z | 150–154° C. |
| 31 | 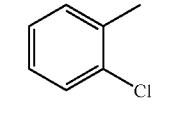 2,4-diCl | O | H | — | — | 200–201° C. |
| 32 | 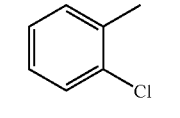 2-Cl | O | H | — | — | 207–209° C. |
| 33 | 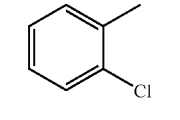 2-Cl | NOH | H | — | E/Z | 160–163° C. |
| 34 | 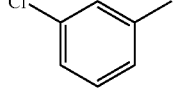 2-Cl | NOMe | H | — | E/Z | 138–140° C. |
| 35 | Cl- (meta) | O | H | — | — | 192–194° C. |

TABLE 1-continued

| Ex | R | Y | R¹ | Salt | Comment | m.p. |
|---|---|---|---|---|---|---|
| 36 | 3-Cl-phenyl | NOH | H | — | E/Z | 188–190° C. |
| 37 | 3-Cl-phenyl | NOMe | H | — | E/Z | 125–127° C. |
| 38 | 4-MeO-phenyl | NOMe | H | — | E/Z | 110–113° C. |
| 39 | 4-Et₂N-phenyl | O | H | — |  | 202° C. |
| 40 | phenyl | O | Ac | — |  | 226° C. |
| 41 | 1-naphthyl | O | H | — |  | 226° C. |
| 42 | 2-naphthyl | O | H | — |  | 180–183° C. |
| 43 | 4-F₃C-phenyl | O | H | — |  | 215–218° C. |
| 44 | 4-Me-phenyl | O | H | — |  | 206–209° C. |
| 45 | 3,4-methylenedioxyphenyl | O | H | — |  | 211–214° C. |

TABLE 1-continued
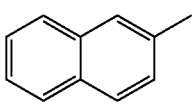
| Ex | R | Y | R¹ | Salt | Comment | m.p. |
|---|---|---|---|---|---|---|
| 46 | 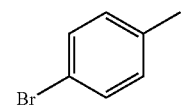 | O | CH₂CH₂CN | — | | 180–182° C. |
| 47 | 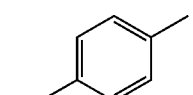 | O | CH₂CH₂CN | — | | 204° C. |
| 48 | 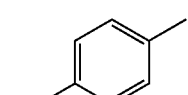 | O | CH₂CH₂CN | — | | 210° C. |
| 49 | 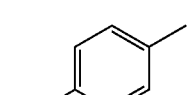 | O | H | — | | 224–227° C. |
| 50 | 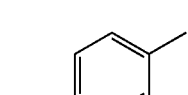 | O | H | — | | 92–96° C. |
| 51 | 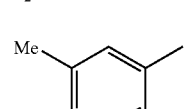 | O | H | HCl | | 227–230° C. |
| 52 | 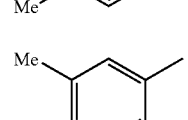 | O | CH₂CH₂CH₂OH | — | | 160–162° C. |
| 53 | 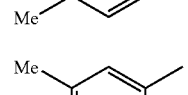 | O | H | — | | 191–194° C. |
| 54 | 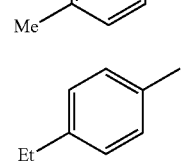 | O | CH₂CH₂CN | — | | 175–178° C. |
| 55 |  | O | H | — | | 208–210° C. |

TABLE 1-continued

| Ex | R | Y | R¹ | Salt | Comment | m.p. |
|---|---|---|---|---|---|---|
| 56 | 4-Et-C₆H₄ | O | CH₂CH₂CN | — | | 180–183° C. |
| 57 | 4-O₂N-C₆H₄ | O | CH₂CH₂CN | — | | 178–181° C. |
| 58 | 4-H₂N-C₆H₄ | O | CH₂CH₂CN | — | | 196–199° C. |
| 59 | pyridin-2-yl | O | H | — | | 179° C. |
| 60 | 4-AcNH-C₆H₄ | O | H | — | | 250° C. |
| 61 | 4-H₂N-C₆H₄ | O | CH₂CH₂CN | (COOH)₂ | | 137–140° C. |
| 62 | 4-H₂N-C₆H₄ | O | H | (COOH)₂ | | 148–150° C. |
| 63 | 4-NC-C₆H₄ | O | H | — | | 242–246° C. |
| 64 | 4-AcNH-3-O₂N-C₆H₃ | O | H | — | | 250–252° C. |
| 65 | 4-H₂N-3-O₂N-C₆H₃ | O | H | — | | >250° C. |

TABLE 1-continued

| Ex | R | Y | R¹ | Salt | Comment | m.p. |
|---|---|---|---|---|---|---|
| 66 | 3-(O₂N), 4-Cl-phenyl | O | H | — | | 198–200° C. |
| 67 | 4-F-phenyl | O | H | — | | 218–220° C. |
| 68 | 3-(O₂N), 4-MeO-phenyl | O | H | — | | 220–223° C. |
| 69 | 3-(H₂N), 4-MeO-phenyl | O | CH₂CH₂CN | — | | 225–226° C. |
| 70 | 6-Cl-pyridin-3-yl | O | H | — | | 190–192° C. |
| 71 | 2,5-diF-phenyl | O | H | — | | 186–188° C. |
| 72 | thien-2-yl | O | H | — | | 205° C. |
| 73 | 3-MeO, 4-BnO-phenyl | O | H | — | | 208–210° C. |
| 74 | 3-MeO, 4-HO-phenyl | O | H | — | | 265° C. |
| 75 | 3-MeO, 4-AcO-phenyl | O | H | — | | 205–208° C. |

TABLE 1-continued

| Ex | R | Y | R¹ | Salt | Comment | m.p. |
|---|---|---|---|---|---|---|
| 76 | 3,4-dimethoxyphenyl (MeO, MeO) | O | H | — | | 244° C. |
| 77 | 4-(2-methoxyethoxy)phenyl | O | H | — | | 174° C. |
| 78 | 2-amino-5-pyridyl | O | H | — | | >250° C. |
| 79 | 2-amino-5-pyridyl | O | CH₂CH₂CN | — | | 223° C. |
| 80 | 2-acetamido-5-pyridyl | O | CH₂CH₂CN | — | | |
| 81 | 3,4-dihydroxyphenyl | O | H | — | | 250° C. |
| 82 | 6-chloro-3-pyridazinyl | O | CH₂CH₂CN | — | | |
| 83 | 3,4-bis(methoxymethoxy)phenyl | O | H | — | | oil |
| 84 | 6-amino-3-pyridazinyl | O | CH₂CH₂CN | — | | |
| 85 | 6-amino-3-pyridazinyl | O | CH₂CH₂CN | HCl | | |

TABLE 1-continued

| Ex | R | Y | R¹ | Salt | Comment | m.p. |
|----|---|---|----|------|---------|------|
| 86 | 5-methyl-2-methoxypyridin-3-yl | O | CH₂CH₂CN | — | | |
| 87 | 5-methyl-2-methoxypyridin-3-yl | O | CH₂CH₂CN | HCl | | |

TABLE 2

| Ex | R | R¹ | Salt | Comment | m.p. |
|----|---|----|------|---------|------|
| 88 | 4-chlorophenyl | H | — | | 162–165° C. |
| 89 | 4-bromophenyl | H | — | | 164–167° C. |
| 90 | 4-methoxyphenyl | H | — | | 156–159° C. |
| 91 | 4-trifluoromethylphenyl | H | — | | 148–150° C. |
| 92 | 3,4-dichlorophenyl | H | — | | 151–153° C. |

TABLE 2-continued

| Ex | R | R¹ | Salt | Comment | m.p. |
|---|---|---|---|---|---|
| 93 | 4-Cl-C₆H₄- | CH₂CH₂CN | — | | 162–165° C. |
| 94 | 4-Br-C₆H₄- | CH₂CH₂CN | — | | 176–179° C. |
| 95 | C₆H₅- | CH₂CH₂CN | — | | 175–178° C. |
| 96 | 4-OHC-C₆H₄- | H | — | | 193–196° C. |
| 97 | 4-HOCH₂-C₆H₄- | H | — | | |
| 98 | 4-O₂N-C₆H₄- | H | — | | 190–193° C. |
| 99 | 4-H₂N-C₆H₄- | H | — | | 110–113° C. |
| 100 | 4-H₂N-C₆H₄- | H | HCl | | 251–252° C. |
| 101 | 2,4-Me₂-C₆H₃- | H | — | | 142–145° C. |
| 102 | 3,5-(CF₃)₂-C₆H₃- | H | — | | 155–158° C. |

TABLE 2-continued

| Ex | R | R¹ | Salt | Comment | m.p. |
|---|---|---|---|---|---|
| 103 | 3-CF₃-phenyl | H | — | | 145–148° C. |
| 104 | 4-Me-phenyl | CH₂CH₂CN | — | | |
| 105 | 3,4-diMe-phenyl | CH₂CH₂CH₂OH | — | | |
| 106 | 6-Cl-pyridin-3-yl | H | — | | |
| 107 | 6-NH₂-pyridin-3-yl | H | — | | |

TABLE 3

| Ex | R | R⁴ | R⁵ | Salt | Comment | m.p. |
|---|---|---|---|---|---|---|
| 108 | phenyl | Me | Me | — | | 250° C. |
| 109 | 4-Br-phenyl | Me | Me | — | | 238° C. |
| 110 | 4-Cl-phenyl | Me | Me | — | | 237° C. |
| 111 | 4-MeO-phenyl | Me | Me | — | | 218–220° C. |

TABLE 3-continued structure with R4, R5 on benzimidazole linked to furazan-NH2, N-CH2-C(=O)-R

| Ex | R | R⁴ | R⁵ | Salt | Comment | m.p. |
|---|---|---|---|---|---|---|
| 112 | 4-Ph-C₆H₄ | Me | Me | — | | 228° C. |
| 113 | C₆H₅ | OMe | OMe | — | | >250° C. |
| 114 | 4-Cl-C₆H₄ | OMe | OMe | — | | >250° C. |
| 115 | 4-Br-C₆H₄ | OMe | OMe | — | | >250° C. |
| 116 | 4-MeO-C₆H₄ | OMe | OMe | — | | >250° C. |
| 117 | 4-Ph-C₆H₄ | OMe | OMe | — | | 238° C. |

TABLE 4 structure with benzimidazole linked to furazan-NH2, N-CH2-C(=O)-CH=CH-R

| Ex | R | Salt | Comment | m.p. |
|---|---|---|---|---|
| 118 | 4-Cl-C₆H₄ | — | E | 194–196° C. |
| 119 | 4-Me-C₆H₄ | — | E | 188–192° C. |
| 120 | 3-MeO-C₆H₄ | — | E | 194–195° C. |

The following compounds from WO 03/066629 are prepared for comparison of their activity in analogy to the examples described hereinbefore:

TABLE 5 structure of benzimidazole-furazan-NH2 with N-R

| Ex | R | MH⁺ |
|---|---|---|
| A | isopropyl (CH(CH₃)₂) | 244 |
| B | cyclopropylmethyl | 256 |

General methods for testing of compounds of the invention:

Example 121

Cell Cultures and Cell Lines

Cell lines are cultured in RPMI-1640 tissue culture medium containing either 5% or 10% fetal calf serum, 0.05 mM 2-mercaptoethanol, 2 mM glutamine and penicillin/streptomycin 50 μg/ml (complete medium) (Sigma, Buchs, Switzerland). General growth conditions are 37° C. and 7.5% $CO_2$.

The following mouse cell lines (either EGFP transfected or not) are being used: A20.2J (ATCC: TIB-208), MC57G (ATCC: CRL-2295).

The following human cell lines (either EGFP transfected or not) are being used: HeLa (ATCC: CCL-2), KB (ATCC:

CCL-17), MCF7 (ATCC: HTB-22), SK-BR-3 (ATCC: HTB-30), SK-Mel 1 (ATCC: HTB-67), SK-Mel 28 (ATCC: HTB-72), PC-3 (ATCC: CRL-1435), SW 480 (ATCC: CCL-228), NCI-H460 (ATCC: HTB-177), NCI-H1792 (ATCC: CRL-5895), HT1080 (ATCC: CCL-21), Jurkat (ATCC: TIB-152), Ramos (ATCC: CRL-1596), Raji (ATCC: CCL-86), H9 (ATCC: HTB-176), Hut78 (ATCC: TIB-161), K562 (ATCC: CCL 243), HL-60 (ATCC: CCL 240), U-87MG (ATCC: HTB-14), HepG2 (ATCC: HB-8065), U-2 OS (ATCC: HTB-96), Saos-2 (ATCC: HTB-85), U937 (ATCC: CRL 1593), Hs 578T (ATCC: HTB 126), HBL-100 (ATCC: HTB 124), Molt-4 (ATCC: CRL 1582).

Example 122

Primary Screening Setup

All the manipulations are performed under sterile conditions. The assays are being performed in commercially available 96 or 384 well flat bottom clear microtiter plates (Greiner, Germany) respectively, which are suitable for tissue culture techniques. A defined number of EGFP transfected adherent test cells (96 well plates: $10^4$-$10^5$, 384 well plates: 1500-$2*10^4$) are plated out 24 hours before treatment either in 75 µl (96 well plates) or 60 µl (384 well plates) complete medium per well in order to ensure appropriate cell spreading. For this purpose a peristaltic pump (e.g. Multidrop by Thermo-Labsystems, Finland) or another suitable device is used. Cells in suspension are plated out according to the same procedure but 1 h prior to treatment. Between seeding out and treatment or addition of compounds the cells are incubated at 37° C. under 7.5% $CO_2$. Subsequently, the compounds under investigation are added at defined concentrations (40-80 µM in either 25 µl (96 well plates) or 20 µl (384 well plates) complete medium containing max 4% DMSO) with an appropriate device (e.g. liquid handling system, multi channel pipette etc.) resulting in a final concentration in the test well of 10-20 µM compound in max 1% DMSO.

Immediately after the addition of the compounds to the cells the zero fluorescence value (t=0 h) is determined by using a fluorescence microplate reader in order to be able to normalize the fluorescence activities. Afterwards, the test plates are further incubated for a total of 48 h at 37° C. under 7.5% $CO_2$ and are shortly removed only for the purpose of measurement at 8 h, 24 h and 48 h, respectively.

Example 123

Measurement and Quantification of the Primary Screening

Relative fluorescence activities of EGFP in compound treated test cells in relation to control cells and cells treated with standard drugs are measured by using a BMG Fluostar microplate fluorescence reader equipped with a filter pair for excitation/emission at 485 nm/520 nm. The optimum signal to noise ratio is detected by using the time-resolved mode of measurement with a delay of 20 µs and an integration time over 1 ms. The gain is adjusted in such a way that the control cells produce a fluorescence activity of 90% of the maximum. Kinetics is performed by measuring the relative fluorescence activities at t=0 h, 8 h, 24 h and 48 h. Crude fluorescence activities are individually normalized for different cell numbers and various optical activities of the test compounds/plate-wells by dividing each value from t=8 h, 24 h and 48 h by the value of t=0 h resulting in E(8), E(24) and E(48) values. Subsequently, the E(x) values are further processed by forming the inverse (Q-value) of the products E(8)*E(24)*E(48) which result in numbers >1 for apoptotic/necrotic activities of the compounds and numbers <1 for proliferative activities of the compounds. Controls (untreated) show values similar to 1. Compounds producing Q values >2 are being considered relevant in terms of apoptotic/necrotic activity and are subsequently tested in the secondary screening setup.

Example 124

Secondary Screening Setup

All the manipulations are performed under sterile conditions. The assays are being performed in case of adherent cells in commercially available 24 well flat bottom tissue culture plates (Greiner, Germany) and in case of suspension cells in polypropylene tubes (P-tubes) 1.4 ml (Matrix, UK), respectively.

Adherent test cells: $2*10^4$-$4*10^4$ of EGFP transfected cells in 0.5 ml complete medium are plated out 24 h before treatment. At t=0 the medium is removed and 450 µl new complete medium is added. Subsequently, 50 µl complete medium containing the test compound in max. 5% DMSO is added resulting in final concentrations of 20 µM, 10 µM, 3 µM, 1 µM and 0.3 µM of the test compounds, respectively. After 48 h incubation the cells are harvested and analyzed with fluorescence activated cell scanning device (FACS Calibur™, BD Biosciences) according to standard procedures.

Suspension cells: $10^5$ test cells in 450 µl complete medium are pipetted into P-tubes. 50 µl complete medium containing the compounds (see adherent cells) is added immediately. After 48 h of incubation the test cells are analyzed directly on a FACSCalibur™.

Example 125

Quantification of the Secondary Screening

By monitoring the EGFP fluorescence activity in FL1 on a FACSCalibur™, it is possible to distinguish between proliferating cells, apoptotic cells and necrotic cells within the same cell population. The proliferating cells show a high GFP fluorescence activity, the apoptotic population shows an intermediate fluorescence activity whereas the necrotic cells demonstrate a residual fluorescence activity comparable to mock-transfected cells. Within the CellQuest Software (BD Biosciences) three regions are defined in the histogram: M1 comprising the proliferating cells, M2 comprising the apoptotic cell population and M3 comprising the necrotic cell population. As readout the relative abundance of the cells belonging either to M1, M2 or M3 are expressed. Compounds inducing M2 values >50% and M3 values <30% are being considered relevant and are further tested and characterized in the tertiary/advanced screening setup.

Example 126

Tertiary Screening Setup

A) Hoechst 33342 Nuclear Staining

This assay is performed in 96 well tissue culture plates. Appropriate number of cells (adherent cells: 3-$5*10^3$, suspension cells: 8-$10*10^3$) are being seeded out in 80 µl complete medium. Adherent cells are incubated for 24 h for proper spreading out before addition of test compounds while suspension cells are immediately treated with test compounds after seeding out. The test compounds are added in 20 µl complete medium containing max 5% DMSO. The final compound concentrations in the assays are 10 µM, 3 µM, 1 µM and 0.3 µM, respectively. After 24 h or 48 h incubation at culture conditions, 10 µl medium containing Hoechst 33342 dye (Sigma B-2261) at 2-5 µg/ml are added to each well. The assay plates are then further incubated for 30 minutes and subsequently analyzed with a standard inverted fluorescence microscope.

The readout allows the determination of the fraction of apoptotic nuclei as well as other morphological criteria specific for apoptosis as a function of the treatment. Results are indicated in Table 6. The following scores are used: 0 relating to no activity, 1 relating to weak activity comprising less than 70% of the cells and score 2 relating to strong activity comprising more than 70% of the cells.

TABLE 6

Hoechst 33342 nuclear staining

| Example | conc | Jurkat | Jily | PBLs | HeLa | H460 | MRC5 |
|---|---|---|---|---|---|---|---|
| 1 | 1 µM | 2 | n.d. | 0 | 2 | 2 | 1 |
|  | 0.1 µM | 0 | n.d. | 0 | 0 | 0 | 0 |
|  | 0.01 µM | 0 | n.d. | 0 | 0 | 0 | 0 |
| 2 | 1 µM | 0 | n.d. | 0 | 0 | 0 | 0 |
|  | 0.1 µM | 0 | n.d. | 0 | 0 | 0 | 0 |
|  | 0.01 µM | 0 | n.d. | 0 | 0 | 0 | 0 |
| 3 | 1 µM | 0 | n.d. | 0 | 0 | n.d. | 0 |
|  | 0.1 µM | 0 | n.d. | 0 | 0 | n.d. | 0 |
|  | 0.01 µM | 0 | n.d. | 0 | 0 | n.d. | 0 |
| 4 | 1 µM | 2 | 2 | 0 | 2 | 1 | 2 |
|  | 0.1 µM | 0 | 0 | 0 | 0 | 0 | 0 |
|  | 0.01 µM | 0 | 0 | 0 | 0 | 0 | 0 |
| 5 | 1 µM | 2 | n.d. | 0 | 2 | n.d. | 0 |
|  | 0.1 µM | 0 | n.d. | 0 | 0 | n.d. | 0 |
|  | 0.01 µM | 0 | n.d. | 0 | 0 | n.d. | 0 |
| 6 | 1 µM | 2 | 2 | 0 | 2 | 2 | 2 |
|  | 0.1 µM | 2 | 2 | 0 | 2 | 2 | 2 |
|  | 0.01 µM | 2 | 2 | 0 | 0 | 0 | 2 |
| 7 | 1 µM | 2 | 2 | 0 | 2 | 2 | 0 |
|  | 0.1 µM | 0 | 0 | 0 | 0 | 0 | 0 |
|  | 0.01 µM | 0 | 0 | 0 | 0 | 0 | 0 |
| 8 | 1 µM | 1 | 0 | 0 | 1 | 0 | 0 |
|  | 0.1 µM | 0 | 0 | 0 | 0 | 0 | 0 |
|  | 0.01 µM | 0 | 0 | 0 | 0 | 0 | 0 |
| 9 | 1 µM | 2 | 2 | 2 | 2 | 0 | 2 |
|  | 0.1 µM | 0 | 0 | 0 | 0 | 0 | 0 |
|  | 0.01 µM | 0 | 0 | 0 | 0 | 0 | 0 |
| 10 | 1 µM | 2 | 2 | 0 | 2 | 2 | 1 |
|  | 0.1 µM | 2 | 1 | 0 | 0 | 1 | 0 |
|  | 0.01 µM | 0 | 0 | 0 | 0 | 0 | 0 |
| 11 | 1 µM | 2 | 2 | 0 | 2 | 2 | 2 |
|  | 0.1 µM | 2 | 2 | 0 | 1 | 0 | 1 |
|  | 0.01 µM | 0 | 0 | 0 | 0 | 0 | 0 |
| 12 | 1 µM | 2 | 2 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 13 | 1 µM | 2 | 2 | 0 | 2 | 2 | 2 |
|  | 0.1 µM | 0 | 0 | 0 | 0 | 0 | 0 |
|  | 0.01 µM | 0 | 0 | 0 | 0 | 0 | 0 |
| 14 | 1 µM | 2 | 2 | 0 | 2 | 2 | 2 |
|  | 0.1 µM | 2 | 2 | 0 | 1 | 2 | 1 |
|  | 0.01 µM | 0 | 0 | 0 | 0 | 0 | 0 |
| 15 | 1 µM | 2 | 2 | 0 | 2 | 2 | 2 |
|  | 0.1 µM | 2 | 2 | 0 | 2 | 2 | 1 |
|  | 0.01 µM | 2 | 2 | 0 | 1 | 2 | 0 |
| 16 | 1 µM | 2 | 2 | 0 | 2 | 2 | 2 |
|  | 0.1 µM | 2 | 2 | 0 | 2 | 2 | 2 |
|  | 0.01 µM | 0 | 0 | 0 | 0 | 0 | 0 |
| 17 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |

TABLE 6-continued

Hoechst 33342 nuclear staining

| Example | conc | Jurkat | Jily | PBLs | HeLa | H460 | MRC5 |
|---|---|---|---|---|---|---|---|
| 18 | 1 µM | 2 | n.d. | 0 | 2 | 1 | 1 |
|  | 0.1 µM | 0 | n.d | 0 | 0 | 0 | 0 |
|  | 0.01 µM | 0 | n.d. | 0 | 0 | 0 | 0 |
| 19 | 1 µM | 2 | 2 | 0 | 2 | 2 | 2 |
|  | 0.1 µM | 2 | 2 | 0 | 1 | 0 | 0 |
|  | 0.01 µM | 0 | 0 | 0 | 0 | 0 | 0 |
| 20 | 1 µM | 0 | n.d. | 0 | 0 | 0 | 0 |
|  | 0.1 µM | 0 | n.d. | 0 | 0 | 0 | 0 |
|  | 0.01 µM | 0 | n.d. | 0 | 0 | 0 | 0 |
| 21 | 1 µM | 0 | n.d. | 0 | 0 | 0 | 0 |
|  | 0.1 µM | 0 | n.d. | 0 | 0 | 0 | 0 |
|  | 0.01 µM | 0 | n.d. | 0 | 0 | 0 | 0 |
| 22 | 1 µM | 2 | n.d. | 0 | 2 | 0 | 0 |
|  | 0.1 µM | 0 | n.d. | 0 | 0 | 0 | 0 |
|  | 0.01 µM | 0 | n.d. | 0 | 0 | 0 | 0 |
| 23 | 1 µM | 2 | n.d. | 0 | 2 | n.d. | 0 |
|  | 0.1 µM | 0 | n.d. | 0 | 0 | n.d. | 0 |
|  | 0.01 µM | 0 | n.d. | 0 | 0 | n.d. | 0 |
| 24 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 25 | 1 µM | 1 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 26 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 27 | 1 µM | 0 | n.d. | 0 | 0 | 0 | 0 |
|  | 0.1 µM | 0 | n.d. | 0 | 0 | 0 | 0 |
|  | 0.01 µM | 0 | n.d. | 0 | 0 | 0 | 0 |
| 28 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 29 | 1 µM | 2 | 2 | 0 | 2 | 2 | 2 |
|  | 0.1 µM | 2 | 2 | 0 | 1 | 0 | 2 |
|  | 0.01 µM | 0 | 0 | 0 | 0 | 0 | 0 |
| 30 | 1 µM | 2 | 1 | 0 | 1 | 0 | 2 |
|  | 0.1 µM | 0 | 0 | 0 | 0 | 0 | 0 |
|  | 0.01 µM | 0 | 0 | 0 | 0 | 0 | 0 |
| 31 | 1 µM | 1 | n.d. | 0 | 0 | 0 | 0 |
|  | 0.1 µM | 0 | n.d. | 0 | 0 | 0 | 0 |
|  | 0.01 µM | 0 | n.d. | 0 | 0 | 0 | 0 |
| 32 | 1 µM | 2 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 33 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 34 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 35 | 1 µM | 2 | 2 | 0 | 2 | 2 | 2 |
|  | 0.1 µM | 2 | 1 | 0 | 0 | 0 | 2 |
|  | 0.01 µM | 0 | 0 | 0 | 0 | 0 | 0 |
| 36 | 1 µM | n.d. | 0 | 0 | 0 | 0 | 0 |
|  | 0.1 µM | n.d. | 0 | 0 | 0 | 0 | 0 |
|  | 0.01 µM | n.d. | 0 | 0 | 0 | 0 | 0 |
| 37 | 1 µM | n.d. | 2 | 0 | 0 | 0 | 1 |
|  | 0.1 µM | n.d. | 0 | 0 | 0 | 0 | 0 |
|  | 0.01 µM | n.d. | 0 | 0 | 0 | 0 | 0 |
| 38 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 39 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 40 | 1 µM | 0 | 1 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 41 | 1 µM | 2 | 2 | 1 | 2 | n.d. | 0 |
|  | 0.1 µM | 0 | 0 | 0 | 0 | n.d. | 0 |
|  | 0.01 µM | 0 | 0 | 0 | 0 | n.d. | 0 |
| 42 | 1 µM | 2 | 2 | 0 | 2 | 2 | 2 |
|  | 0.1 µM | 2 | 2 | 0 | 1 | 2 | 2 |
|  | 0.01 µM | 0 | 0 | 0 | 0 | 0 | 0 |

TABLE 6-continued

Hoechst 33342 nuclear staining

| Example | conc | Jurkat | Jily | PBLs | HeLa | H460 | MRC5 |
|---|---|---|---|---|---|---|---|
| 43 | 1 μM | 2 | 1 | 0 | 1 | n.d. | 1 |
|  | 0.1 μM | 0 | 0 | 0 | 0 | n.d. | 0 |
|  | 0.01 μM | 0 | 0 | 0 | 0 | n.d. | 0 |
| 44 | 1 μM | 2 | 2 | 0 | 2 | 2 | 2 |
|  | 0.1 μM | 2 | 2 | 0 | 1 | 2 | 0 |
|  | 0.01 μM | 0 | 0 | 0 | 0 | 0 | 0 |
| 45 | 1 μM | 2 | 2 | 0 | 2 | 2 | 2 |
|  | 0.1 μM | 2 | 2 | 0 | 1 | 2 | 0 |
|  | 0.01 μM | 0 | 0 | 0 | 0 | 0 | 0 |
| 46 | 1 μM | 2 | 2 | 0 | 2 | 2 | 2 |
|  | 0.1 μM | 2 | 2 | 0 | 0 | 0 | 0 |
|  | 0.01 μM | 0 | 0 | 0 | 0 | 0 | 0 |
| 47 | 1 μM | 2 | 2 | 0 | 2 | 2 | 2 |
|  | 0.1 μM | 2 | 2 | 0 | 2 | 2 | 2 |
|  | 0.01 μM | 2 | 0 | 0 | 0 | 0 | 0 |
| 48 | 1 μM | 2 | 2 | 0 | 2 | 2 | 2 |
|  | 0.1 μM | 2 | 2 | 0 | 2 | 0 | 2 |
|  | 0.01 μM | 0 | 0 | 0 | 0 | 0 | 0 |
| 49 | 1 μM | 2 | 1 | 0 | 1 | 0 | 0 |
|  | 0.1 μM | 0 | 0 | 0 | 0 | 0 | 0 |
|  | 0.01 μM | 0 | 0 | 0 | 0 | 0 | 0 |
| 50 | 1 μM | 2 | 2 | 0 | 2 | 2 | 2 |
|  | 0.1 μM | 2 | 2 | 0 | 2 | 2 | 2 |
|  | 0.01 μM | 2 | 2 | 0 | 0 | 1 | 0 |
| 51 | 1 μM | 2 | 2 | 0 | 2 | 2 | 2 |
|  | 0.1 μM | 2 | 2 | 0 | 2 | 2 | 2 |
|  | 0.01 μM | 1 | 0 | 0 | 0 | 0 | 0 |
| 52 | 1 μM | 2 | 2 | 0 | 2 | 2 | 2 |
|  | 0.1 μM | 2 | 2 | 0 | 2 | 1 | 2 |
|  | 0.01 μM | 0 | 0 | 0 | 0 | 0 | 0 |
| 53 | 1 μM | 2 | 2 | 0 | 2 | 2 | 2 |
|  | 0.1 μM | 2 | 2 | 0 | 2 | 2 | 2 |
|  | 0.01 μM | 2 | 0 | 0 | 0 | 0 | 1 |
| 54 | 1 μM | 2 | 2 | 0 | 2 | 2 | 2 |
|  | 0.1 μM | 2 | 2 | 0 | 2 | 2 | 2 |
|  | 0.01 μM | 1 | 1 | 0 | 0 | 0 | 0 |
| 55 | 1 μM | 2 | 2 | 0 | 2 | 2 | 0 |
|  | 0.1 μM | 1 | 0 | 0 | 0 | 0 | 0 |
|  | 0.01 μM | 0 | 0 | 0 | 0 | 0 | 0 |
| 56 | 1 μM | 2 | 2 | 0 | 2 | 2 | 1 |
|  | 0.1 μM | 2 | 2 | 0 | 1 | 0 | 1 |
|  | 0.01 μM | 0 | 0 | 0 | 0 | 0 | 0 |
| 57 | 1 μM | 2 | 2 | 0 | 2 | 0 | 2 |
|  | 0.1 μM | 0 | 0 | 0 | 0 | 0 | 0 |
|  | 0.01 μM | 0 | 0 | 0 | 0 | 0 | 0 |
| 58 | 1 μM | 2 | 2 | 0 | 2 | 2 | 2 |
|  | 0.1 μM | 2 | 2 | 0 | 2 | 2 | 2 |
|  | 0.01 μM | 2 | 2 | 0 | 2 | 2 | 1 |
| 59 | 1 μM | 2 | 2 | 0 | 2 | 2 | 2 |
|  | 0.1 μM | 0 | 0 | 0 | 0 | 0 | 0 |
|  | 0.01 μM | 0 | 0 | 0 | 0 | 0 | 0 |
| 60 | 1 μM | 2 | 2 | 0 | 1 | 0 | 2 |
|  | 0.1 μM | 0 | 0 | 0 | 0 | 0 | 0 |
|  | 0.01 μM | 0 | 0 | 0 | 0 | 0 | 0 |
| 61 | 1 μM | 2 | 2 | 0 | 2 | 2 | 2 |
|  | 0.1 μM | 2 | 2 | 0 | 2 | 2 | 2 |
|  | 0.01 μM | 0 | 0 | 0 | 0 | 0 | 0 |
| 62 | 1 μM | 2 | 2 | 0 | 2 | 2 | 2 |
|  | 0.1 μM | 2 | 2 | 0 | 2 | 2 | 2 |
|  | 0.01 μM | 0 | 0 | 0 | 0 | 0 | 0 |
| 63 | 1 μM | 0 | 0 | 0 | 0 | 0 | 0 |
|  | 0.1 μM | 0 | 0 | 0 | 0 | 0 | 0 |
|  | 0.01 μM | 0 | 0 | 0 | 0 | 0 | 0 |
| 64 | 1 μM | 2 | 2 | 0 | 2 | 2 | 1 |
|  | 0.1 μM | 2 | 2 | 0 | 2 | 2 | 1 |
|  | 0.01 μM | 2 | 2 | 0 | 0 | 0 | 0 |
| 65 | 1 μM | 2 | 2 | 0 | 2 | 2 | 2 |
|  | 0.1 μM | 2 | 2 | 0 | 2 | 2 | 2 |
|  | 0.01 μM | 2 | 2 | 0 | 0 | 2 | 0 |
| 66 | 1 μM | 2 | 2 | 0 | 2 | 2 | 1 |
|  | 0.1 μM | 1 | 0 | 0 | 0 | 0 | 0 |
|  | 0.01 μM | 0 | 0 | 0 | 0 | 0 | 0 |
| 67 | 1 μM | 2 | 2 | 0 | 2 | 2 | 1 |
|  | 0.1 μM | 2 | 2 | 0 | 0 | 0 | 0 |
|  | 0.01 μM | 0 | 0 | 0 | 0 | 0 | 0 |
| 68 | 1 μM | 2 | 1 | 0 | 2 | 2 | 1 |
|  | 0.1 μM | 2 | 1 | 0 | 0 | 0 | 0 |
|  | 0.01 μM | 0 | 0 | 0 | 0 | 0 | 0 |
| 69 | 1 μM | 2 | 2 | 0 | 2 | 2 | 1 |
|  | 0.1 μM | 1 | 1 | 0 | 0 | 0 | 0 |
|  | 0.01 μM | 0 | 0 | 0 | 0 | 0 | 0 |
| 70 | 1 μM | 2 | 2 | 0 | 2 | 2 | 2 |
|  | 0.1 μM | 2 | 2 | 0 | 2 | 2 | 2 |
|  | 0.01 μM | 2 | 2 | 0 | 0 | 1 | 1 |
| 71 | 1 μM | 2 | 1 | 0 | 0 | 0 | 0 |
|  | 0.1 μM | 0 | 0 | 0 | 0 | 0 | 0 |
|  | 0.01 μM | 0 | 0 | 0 | 0 | 0 | 0 |
| 72 | 1 μM | 2 | 2 | 0 | 2 | 2 | 2 |
|  | 0.1 μM | 1 | 0 | 0 | 0 | 0 | 0 |
|  | 0.01 μM | 0 | 0 | 0 | 0 | 0 | 0 |
| 73 | 1 μM | 2 | 1 | 0 | 1 | 2 | 1 |
|  | 0.1 μM | 0 | 0 | 0 | 0 | 0 | 0 |
|  | 0.01 μM | 0 | 0 | 0 | 0 | 0 | 0 |
| 74 | 1 μM | 2 | 2 | 0 | 2 | 2 | 1 |
|  | 0.1 μM | 0 | 0 | 0 | 0 | 0 | 0 |
|  | 0.01 μM | 0 | 0 | 0 | 0 | 0 | 0 |
| 75 | 1 μM | 2 | 2 | 0 | 1 | 2 | 1 |
|  | 0.1 μM | 0 | 0 | 0 | 0 | 0 | 0 |
|  | 0.01 μM | 0 | 0 | 0 | 0 | 0 | 0 |
| 76 | 1 μM | 2 | 2 | 0 | 2 | 2 | 1 |
|  | 0.1 μM | 2 | 2 | 0 | 0 | 1 | 0 |
|  | 0.01 μM | 0 | 0 | 0 | 0 | 0 | 0 |
| 77 | 1 μM | 2 | 2 | 0 | 2 | 2 | 1 |
|  | 0.1 μM | 0 | 0 | 0 | 0 | 0 | 0 |
|  | 0.01 μM | 0 | 0 | 0 | 0 | 0 | 0 |
| 78 | 1 μM | 2 | 2 | 0 | 2 | 2 | 2 |
|  | 0.1 μM | 2 | 2 | 0 | 2 | 2 | 2 |
|  | 0.01 μM | 2 | 2 | 0 | 2 | 2 | 1 |
| 79 | 1 μM | 2 | 2 | 0 | 2 | 2 | 2 |
|  | 0.1 μM | 2 | 2 | 0 | 2 | 2 | 2 |
|  | 0.01 μM | 2 | 2 | 0 | 2 | 2 | 1 |
| 80 | 1 μM |  |  |  |  |  |  |
|  | 0.1 μM |  |  |  |  |  |  |
|  | 0.01 μM |  |  |  |  |  |  |
| 81 | 1 μM |  |  |  |  |  |  |
|  | 0.1 μM |  |  |  |  |  |  |
|  | 0.01 μM |  |  |  |  |  |  |
| 82 | 1 μM |  |  |  |  |  |  |
|  | 0.1 μM |  |  |  |  |  |  |
|  | 0.01 μM |  |  |  |  |  |  |
| 83 | 1 μM |  |  |  |  |  |  |
|  | 0.1 μM |  |  |  |  |  |  |
|  | 0.01 μM |  |  |  |  |  |  |
| 84 | 1 μM |  |  |  |  |  |  |
|  | 0.1 μM |  |  |  |  |  |  |
|  | 0.01 μM |  |  |  |  |  |  |
| 85 | 1 μM |  |  |  |  |  |  |
|  | 0.1 μM |  |  |  |  |  |  |
|  | 0.01 μM |  |  |  |  |  |  |
| 86 | 1 μM |  |  |  |  |  |  |
|  | 0.1 μM |  |  |  |  |  |  |
|  | 0.01 μM |  |  |  |  |  |  |
| 87 | 1 μM |  |  |  |  |  |  |
|  | 0.1 μM |  |  |  |  |  |  |
|  | 0.01 μM |  |  |  |  |  |  |
| 88 | 1 μM | 2 | 1 | 0 | 2 | n.d. | 0 |
|  | 0.1 μM | 0 | 0 | 0 | 0 | n.d. | 0 |
|  | 0.01 μM | 0 | 0 | 0 | 0 | n.d. | 0 |
| 89 | 1 μM | 2 | 2 | 0 | 2 | 2 | 2 |
|  | 0.1 μM | 2 | 2 | 0 | 2 | 2 | 2 |
|  | 0.01 μM | 0 | 0 | 0 | 0 | 0 | 0 |
| 90 | 1 μM | 2 | 1 | 0 | 1 | n.d. | 1 |
|  | 0.1 μM | 0 | 0 | 0 | 0 | n.d. | 0 |
|  | 0.01 μM | 0 | 0 | 0 | 0 | n.d. | 0 |
| 91 | 1 μM | 2 | 2 | 0 | 0 | n.d. | 0 |
|  | 0.1 μM | 0 | 0 | 0 | 0 | n.d. | 0 |
|  | 0.01 μM | 0 | 0 | 0 | 0 | n.d. | 0 |
| 92 | 1 μM | 2 | 2 | 0 | 2 | 2 | 2 |
|  | 0.1 μM | 2 | 2 | 0 | 2 | 2 | 2 |
|  | 0.01 μM | 0 | 0 | 0 | 0 | 0 | 0 |

TABLE 6-continued

Hoechst 33342 nuclear staining

| Example | conc | Jurkat | Jily | PBLs | HeLa | H460 | MRC5 |
|---|---|---|---|---|---|---|---|
| 93 | 1 µM | 2 | 2 | 0 | 2 | 2 | 2 |
|  | 0.1 µM | 2 | 2 | 0 | 0 | 1 | 0 |
|  | 0.01 µM | 0 | 0 | 0 | 0 | 0 | 0 |
| 94 | 1 µM | 2 | 2 | 0 | 2 | 2 | 2 |
|  | 0.1 µM | 2 | 2 | 0 | 1 | 2 | 0 |
|  | 0.01 µM | 0 | 0 | 0 | 0 | 0 | 0 |
| 95 | 1 µM | 2 | 1 | 0 | 1 | n.d. | 0 |
|  | 0.1 µM | 0 | 0 | 0 | 0 | n.d. | 0 |
|  | 0.01 µM | 0 | 0 | 0 | 0 | n.d. | 0 |
| 96 | 1 µM | 2 | 2 | 0 | 2 | 1 | 0 |
|  | 0.1 µM | 0 | 0 | 0 | 0 | 0 | 0 |
|  | 0.01 µM | 0 | 0 | 0 | 0 | 0 | 0 |
| 97 | 1 µM | 2 | 2 | 0 | 2 | 2 | 0 |
|  | 0.1 µM | 0 | 0 | 0 | 0 | 0 | 0 |
|  | 0.01 µM | 0 | 0 | 0 | 0 | 0 | 0 |
| 98 | 1 µM | 2 | 2 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 99 | 1 µM | 1 | 1 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 100 | 1 µM | 1 | 1 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 101 | 1 µM | 2 | 2 | 0 | 2 | 2 | 1 |
|  | 0.1 µM | 2 | 1 | 0 | 1 | 1 | 1 |
|  | 0.01 µM | 0 | 0 | 0 | 0 | 0 | 0 |
| 102 | 1 µM | 2 | 1 | 0 | 0 | 1 | 0 |
|  | 0.1 µM | 0 | 0 | 0 | 0 | 0 | 0 |
|  | 0.01 µM | 0 | 0 | 0 | 0 | 0 | 0 |
| 103 | 1 µM | 2 | 2 | 0 | 2 | 2 | 1 |
|  | 0.1 µM | 1 | 0 | 0 | 0 | 0 | 0 |
|  | 0.01 µM | 0 | 0 | 0 | 0 | 0 | 0 |
| 104 | 1 µM |  |  |  |  |  |  |
|  | 0.1 µM |  |  |  |  |  |  |
|  | 0.01 µM |  |  |  |  |  |  |
| 105 | 1 µM |  |  |  |  |  |  |
|  | 0.1 µM |  |  |  |  |  |  |
|  | 0.01 µM |  |  |  |  |  |  |
| 106 | 1 µM |  |  |  |  |  |  |
|  | 0.1 µM |  |  |  |  |  |  |
|  | 0.01 µM |  |  |  |  |  |  |
| 107 | 1 µM |  |  |  |  |  |  |
|  | 0.1 µM |  |  |  |  |  |  |
|  | 0.01 µM |  |  |  |  |  |  |
| 108 | 1 µM | 2 | 2 | 0 | 0 | 1 | 0 |
|  | 0.1 µM | 0 | 0 | 0 | 0 | 0 | 0 |
|  | 0.01 µM | 0 | 0 | 0 | 0 | 0 | 0 |
| 109 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 110 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 111 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 112 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 113 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 114 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 115 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 116 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 117 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 118 | 1 µM | 0 | 1 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 119 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| 120 | 1 µM | 0 | 0 | 0 | 0 | 0 | 0 |
|  | 0.1 µM | 0 | 0 | 0 | 0 | 0 | 0 |
|  | 0.01 µM | 0 | 0 | 0 | 0 | 0 | 0 |
| A | 30 µM | 0 | 0 | 0 | 0 | 0 | 0 |
|  | 10 µM | 0 | 0 | 0 | 0 | 0 | 0 |
|  | 3 µM | 0 | 0 | 0 | 0 | 0 | 0 |
| B | 30 µM | 0 | 0 | 0 | 0 | 0 | 0 |
|  | 10 µM | 0 | 0 | 0 | 0 | 0 | 0 |
|  | 3 µM | 0 | 0 | 0 | 0 | 0 | 0 |

0: no effect
1: weak effect
2: strong effect

B) MTS Proliferation Assay

The assay is performed in 96 well tissue culture plates. The cells (range: $1.5*10^3$-$10^4$) are seeded out in 80 µl complete medium 24 h prior to compound treatment. The test compounds are added in 20 µl complete medium containing max 5% DMSO. The final compound concentrations in the assays are 10 µM, 3 µM, 1 µM and 0.3 µM, respectively. The assay plates are incubated for 72 h at culture conditions. The MTS reagent is prepared according to the manufacturer's protocol (Promega G1111). 20 µl MTS reagent are added to each well, the assay plates are quickly spun and incubated for another 3 h at culture conditions. Subsequently, the plates are shortly shaked and absorption measured with a microplate-reader at 492 nm. $IC_{50}$ values are determined by graphical analysis and are indicated in the Table 7 in µM concentration.

TABLE 7

MTS proliferation assay

| | IC 50 | | | | |
|---|---|---|---|---|---|
| No | Jurkat | Jily | HT1080 | HeLa | MRC5 |
| 1 | 2 | n.d. | n.d. | 1 | 0 |
| 2 | 0 | n.d. | n.d. | 0 | 0 |
| 3 | 1 | n.d. | n.d. | n.d. | 0 |
| 4 | 2 | 1 | 1 | 1 | 1 |
| 5 | 1 | n.d. | n.d. | 1 | 1 |
| 6 | 3 | 2 | 2 | 2 | 1 |
| 7 | 1 | 1 | 1 | 1 | 1 |
| 8 | 1 | 1 | 1 | 1 | 1 |
| 9 | 1 | 1 | 1 | 1 | 1 |
| 10 | n.d. | 2 | n.d. | 1 | n.d. |
| 11 | n.d. | 2 | n.d. | 1 | n.d. |
| 12 | 1 | 1 | 0 | 0 | 0 |
| 13 | 1 | 1 | 1 | 1 | 1 |
| 14 | 2 | 2 | 2 | 2 | 2 |
| 15 | 3 | 3 | 3 | 2 | 3 |
| 16 | 1 | 2 | 2 | 1 | 2 |
| 17 | 0 | n.d. | n.d. | 0 | n.d. |
| 18 | 1 | n.d. | n.d. | 0 | 1 |
| 19 | 2 | n.d. | n.d. | 1 | 1 |
| 20 | 1 | n.d. | n.d. | 0 | 0 |
| 21 | 0 | n.d. | n.d. | 0 | 0 |
| 22 | 1 | n.d. | n.d. | 1 | 1 |
| 23 | 1 | n.d. | n.d. | 1 | 1 |
| 24 | 0 | n.d. | n.d. | 0 | 0 |
| 25 | 1 | n.d. | n.d. | 0 | 0 |

TABLE 7-continued

MTS proliferation assay

IC 50

| No | Jurkat | Jily | HT1080 | HeLa | MRC5 |
|---|---|---|---|---|---|
| 26 | 0 | n.d. | n.d. | 0 | 0 |
| 27 | 0 | n.d. | n.d. | 0 | 0 |
| 28 | 0 | n.d. | n.d. | 0 | 0 |
| 29 | 2 | n.d. | n.d. | 2 | 2 |
| 30 | 1 | n.d. | n.d. | 1 | 1 |
| 31 | 1 | 1 | 0 | 1 | 1 |
| 32 | 1 | n.d. | n.d. | 1 | 0 |
| 33 | 0 | n.d. | n.d. | 0 | 0 |
| 34 | 0 | n.d. | n.d. | 0 | 0 |
| 35 | 2 | 2 | 1 | 2 | 1 |
| 36 | 2 | 2 | 1 | 2 | 1 |
| 37 | 1 | n.d. | n.d. | 1 | 1 |
| 38 | 1 | n.d. | n.d. | 1 | 0 |
| 39 | 0 | n.d. | n.d. | 0 | 0 |
| 40 | 1 | n.d. | n.d. | 1 | 0 |
| 41 | 1 | 1 | 1 | 1 | 1 |
| 42 | 2 | 2 | 2 | 2 | 1 |
| 43 | 1 | 1 | 1 | 1 | 1 |
| 44 | 3 | 2 | 2 | 2 | 2 |
| 45 | 2 | 2 | 2 | 2 | 1 |
| 46 | 3 | 2 | 2 | 2 | 1 |
| 47 | 3 | 3 | 2 | 2 | 1 |
| 48 | 3 | 2 | 2 | 2 | 2 |
| 49 | 1 | 1 | 0 | 0 | 0 |
| 50 | 2 | 2 | 2 | 2 | 2 |
| 51 | 2 | 2 | 2 | 2 | 2 |
| 52 | n.d. | 2 | n.d. | 2 | n.d. |
| 53 | n.d. | 2 | n.d. | 2 | n.d. |
| 54 | n.d. | 2 | 2 | 2 | 2 |
| 55 | n.d. | 2 | 1 | 1 | 1 |
| 56 | n.d. | 2 | 2 | 2 | 2 |
| 57 | 2 | 2 | 1 | 1 | 1 |
| 58 | 3 | 3 | 3 | 2 | 3 |
| 59 | 1 | 1 | 1 | 1 | 1 |
| 60 | 1 | 1 | 1 | 1 | 1 |
| 61 | 2 | 2 | 2 | 2 | 2 |
| 62 | 2 | 2 | 2 | 1 | 2 |
| 63 | 0 | n.d. | 0 | 0 | 0 |
| 64 | 2 | 2 | 2 | 2 | 2 |
| 65 | 3 | 3 | 3 | 2 | 3 |
| 66 | 2 | 1 | 1 | 1 | 1 |
| 67 | 1 | 2 | 1 | 1 | 1 |
| 68 | 2 | 2 | 1 | 1 | 1 |
| 69 | 2 | 1 | 1 | 1 | 1 |
| 70 | 3 | 3 | 3 | 3 | 3 |
| 71 | n.d. | 1 | 0 | 1 | 0 |
| 72 | 1 | 1 | 1 | 1 | 1 |
| 73 | 1 | 1 | 1 | 1 | 1 |
| 74 | 1 | 1 | 1 | 1 | 1 |
| 75 | 1 | 1 | 1 | 1 | 1 |
| 76 | 1 | 2 | 1 | 1 | 1 |
| 77 | 1 | 1 | 1 | 1 | 1 |
| 78 | 3 | 3 | 3 | 3 | 3 |
| 79 | 3 | 3 | 3 | 3 | 3 |
| 80 | | | | | |
| 81 | | | | | |
| 82 | | | | | |
| 83 | | | | | |
| 84 | | | | | |
| 85 | | | | | |
| 86 | | | | | |
| 87 | | | | | |
| 88 | 1 | 1 | 1 | 1 | 1 |
| 89 | 2 | 2 | 2 | 2 | 1 |
| 90 | 1 | 1 | 1 | 1 | 1 |
| 91 | 1 | 1 | 1 | 1 | 1 |
| 92 | 2 | 2 | 2 | 2 | 1 |
| 93 | 2 | 2 | 1 | 1 | 1 |
| 94 | 2 | 2 | 2 | 2 | 1 |
| 95 | 1 | 1 | 1 | 1 | 1 |
| 96 | 1 | 1 | 1 | 1 | 1 |
| 97 | 1 | 1 | 1 | 1 | 1 |
| 98 | 1 | 1 | 0 | 0 | 0 |
| 99 | 1 | 1 | 0 | 0 | 0 |
| 100 | 1 | 0 | 0 | 0 | 0 |
| 101 | n.d. | 2 | 2 | 2 | 2 |
| 102 | n.d. | 1 | 0 | 0 | 1 |
| 103 | n.d. | 2 | 1 | 1 | 1 |
| 104 | | | | | |
| 105 | | | | | |
| 106 | | | | | |
| 107 | | | | | |
| 108 | 1 | 1 | 1 | 1 | 1 |
| 109 | 1 | n.d. | n.d. | 0 | 0 |
| 110 | 0 | n.d. | 0 | 0 | 0 |
| 111 | 0 | n.d. | 0 | 0 | 0 |
| 112 | 0 | n.d. | 0 | 0 | 0 |
| 113 | 0 | n.d. | 0 | 0 | 0 |
| 114 | 0 | n.d. | 0 | 0 | 0 |
| 115 | 0 | n.d. | 0 | 0 | 0 |
| 116 | 0 | n.d. | 0 | 0 | 0 |
| 117 | 0 | n.d. | 0 | 0 | 0 |
| 118 | 0 | 0 | 0 | 0 | 0 |
| 119 | 0 | 0 | 0 | 0 | 0 |
| 120 | 0 | 0 | 0 | 0 | 0 |
| A | 0 | 0 | 0 | 0 | 0 |
| B | 0 | 0 | 0 | 0 | 0 |

0 IC 50 > 1 µM
1 0.1 µM < IC 50 < 1 µM
2 0.01 < IC 50 < 0.1 µM
3 IC 50 < 0.01 µM

C) Annexin V/7-AAD Staining

Adherent cells (1-2*$10^5$) are 24 h prior to compound treatment seeded into 24 well tissue culture plates. Suspension cells are pipetted into P-tubes immediately before treatment. Test compounds are added leading to a final concentrations of 10 µM. After 24 h Treatment cells are harvested (in case of adherent cells by trypsinization) and transferred to FACS tubes (BD Biosciences). After centrifugation and removal of the supernatant, 100 µl complete medium containing AnnexinV-GST (10 µg) is added, mixed and incubated at 4° C. for 30 minutes. Subsequently, the cells are washed once with medium and incubated with 100 µl anti-GST Alexa 488 (Molecular Probes A-11131) in medium diluted 1:500 for 30 minutes at 4° C. Then, cells are washed once and stained with 1 µg/ml 7-aminoactino-mycin D (7-AAD) (Molecular Probes A-1310) in 250 µl medium and analyzed on the FACSCalibur™. AnnexinV is measured in FL1 whereas 7-AAD is measured in FL3.

D) PI Staining for Cell Cycle Distribution 1-2*$10^5$ cells are seeded into 24 well tissue culture plates and incubated for 24 h prior to compound addition. Compounds are added for 24 h in a final concentration of 3 µM or 10 µM. Adherent cells are harvested by trypsinization. The cell suspensions are fixed by adding 2 parts ice cold ethanol 100% while vortexing. Then the samples are stored for >2 h at −20° C. Subsequently the cells are washed with PBS once and resuspended in 250 µl PBS containing 50 µg/ml PI (Calbiochem # 537059), then the samples are incubated at 37° C. for 30 minutes and subsequently analyzed on a FACSCalibur™ monitoring linear PI fluorescence activity on FL2. The readout allows the detection of a possible direct or indirect influence of the tested compounds on the cell cycle. The following events can occur: a) Generation of a subG1 peak indicative for DNA fragmentation, b) increase of the cell population arrested in G2M phase. Both events are scored by 1 for weak and 2 for strong occurrence. 0 indicates no occurrence at all. In Table 8 the influences of several tested compounds are demonstrated.

TABLE 8

Pl staining for cell cycle distribution

| | Jurkat 3 μM | | HeLa 10 μM | |
|---|---|---|---|---|
| No | subG1 | G2M | subG1 | G2M |
| 16 | 0 | 0 | 0 | 2 |
| 19 | 0 | 0 | 0 | 2 |
| 29 | 0 | 0 | 0 | 2 |
| 30 | 0 | 0 | 0 | 2 |
| 58 | 0 | 0 | 0 | 2 |

0: no effect
1: weak effect
2: strong effect

E) BrdU Incorporation (Proliferation)

Adherent cells are seeded out at 2-4*10$^4$ cells/well/ml in 24 well tissue culture plates 24 h prior to treatment. Suspension cells are seeded out at 2*10$^5$ cells/ml/well in 24 well plates. Compounds are added leading to final concentrations of 3 μM and 10 μM, respectively. Subsequently, BrdU (Molecular Probes #B-23151) at 10 μM final concentration is added and the plates are incubated for 48 h. After the incubation cells are processed according to standard procedures. The detection of the incorporated BrdU is done with the anti-bromodeoxyuridine Mab PRB-1, Alexa Fluor 660 conjugate (Molecular Probes #A-21306). The analysis is performed on a FACSCalibur™ by monitoring the fluorescence activity on FL3. The readout reflects DNA synthesis which is a hallmark for proliferation.

F) Caspase Dependencies

Caspase dependencies are being evaluated by combining the compound treatment with the pan-caspase inhibitor ZVAD or its control peptide zFA (ICN Pharmaceuticals # FK009 and FK029, respectively). Both peptides are being used at 20 μM concentration. In case of caspase dependencies a clear inhibition of the specific readout in all apoptosis tests should be detected. By comparing the readout of zVAD and zFA treated samples with the compound control it is possible to detect caspase resp. cystein proteinase dependencies. In case of inhibition by ZVAD but not by zFA a clear caspase dependency is obvious. An inhibition by zVAD as well as by zFA points towards the involvement of cystein proteinases In the apoptotic cascade. Table 9 demonstrates the protease dependency of the nuclear fragmentation visualized by Hoechst 33342 staining.

Example 127

Soft Capsules 5000 soft gelatin capsules, each comprising as active ingredient 0.05 g of one of the compounds of formula (I) mentioned in the preceding Examples, are prepared as follows: 250 g pulverized active ingredient is suspended in 2 liter Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:

1. A compound of the formula

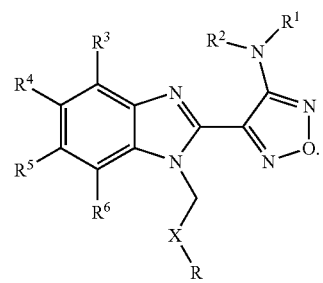

(I)

wherein

R represents phenyl, naphthyl, thienyl, pyridinyl or pyridazinyl ring, said phenyl ring being optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy lower alkoxy, phenyl-lower alkoxy, lower alkylcarbonyloxy, amino, monoalkylamino, dialkylamino, lower alkoxycarbonylamino, lower alkycarbonylamino, substituted amino wherein the two substituents on nitrogen form together with the nitrogen a heterocyclcyl, lower alkylcarbonyl, formyl, carboxy, lower alkoxycarbonyl, cyano, halogen, and nitro;

and wherein two adjacent substituents are methylenedioxy;

and said pyridinyl or pyridazinyl being optionally substituted in one or two positions with lower alkoxy, amino, or halogen;

X is —O— or >C=Y, wherein Y is oxygen;

R$^1$ represents hydrogen, hydroxy-lower alkyl, cyano-lower alkyl or lower alkyl-carbonyl, and R$^2$, R$^3$, R$^4$, R$^5$ and R$^6$ is hydrogen;

or a pharmaceutically acceptable salt thereof.

2. The compound of claim 1 where X is >C=Y, wherein Y is oxygen, or it's pharmaceutically acceptable salts.

3. The compound of claim 2, which compounds are selected from the group consisting of the compounds 1, 5, 6, 11, 14, 15, 16, 19, 23, 29, 35, 41, 42, 44, 45, 46, 47, 48, 50, 52, 53, 54, 55, 56, 57, 58, 59, 61, 62, 64, 65, 66, 67, 68, 69, 70, 72, 74, 76, 77, 78 and 79, which compounds are set forth according to the following table:

| Compound | R | R$^1$ |
|---|---|---|
| 1 | ⌬ phenyl | H |
| 5 | 4-Cl-phenyl | (CO)CH$_3$ |
| 6 | 4-Cl-phenyl | CH$_2$CH$_2$CN |

-continued
| Compound | R | R¹ |
|---|---|---|
| 11 | 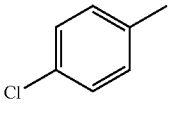 | CH₂CH₂CH₂OH |
| 14 | 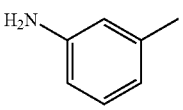 | H |
| 15 | 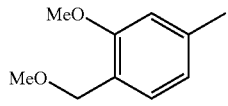 | H |
| 16 | 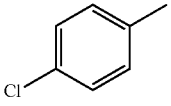 | H |
| 19 | 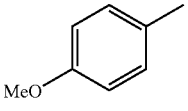 | H |
| 23 | 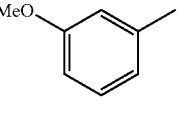 | H |
| 29 | 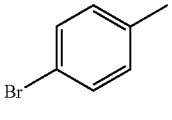 | H |
| 35 | 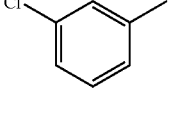 | H |
| 41 | 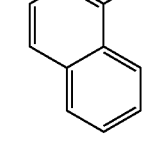 | H |
| 42 | 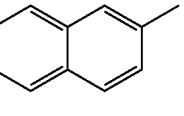 | H |
| 44 | 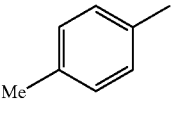 | H |
| 45 | 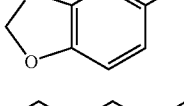 | H |
| 46 | 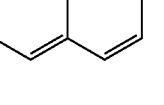 | CH₂CH₂CN |
-continued
| Compound | R | R¹ |
|---|---|---|
| 47 | 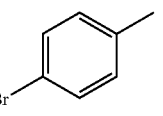 | CH₂CH₂CN |
| 48 | 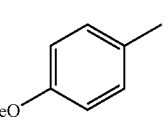 | CH₂CH₂CN |
| 50 | 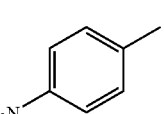 | H |
| 52 | 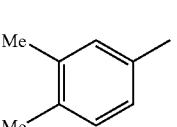 | CH₂CH₂CH₂OH |
| 53 | 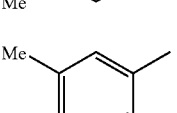 | H |
| 54 | 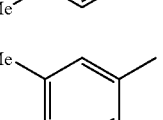 | CH₂CH₂CN |
| 55 | 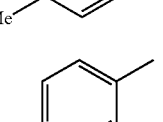 | H |
| 56 | 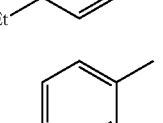 | CH₂CH₂CN |
| 57 | 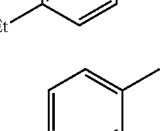 | CH₂CH₂CN |
| 58 | 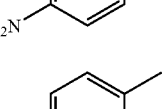 | CH₂CH₂CN |
| 59 | 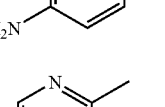 | H |
| 61 | 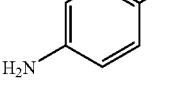 | CH₂CH₂CN |

-continued

| Compound | R | R¹ |
|---|---|---|
| 62 | 4-aminophenyl (H₂N-C₆H₄-) | H |
| 64 | 4-acetamido-3-nitrophenyl (O₂N, AcHN substituted phenyl) | H |
| 65 | 4-amino-3-nitrophenyl (O₂N, H₂N substituted phenyl) | H |
| 66 | 4-chloro-3-nitrophenyl (O₂N, Cl substituted phenyl) | H |
| 67 | 4-fluorophenyl | H |
| 68 | 4-methoxy-3-nitrophenyl (O₂N, MeO substituted phenyl) | H |
| 69 | 3-amino-4-methoxyphenyl (H₂N, MeO substituted phenyl) | CH₂CH₂CN |
| 70 | 6-chloropyridin-3-yl | H |
| 72 | thiophen-2-yl | H |
| 74 | 4-hydroxy-3-methoxyphenyl (MeO, HO substituted phenyl) | H |
| 76 | 3,4-dimethoxyphenyl (MeO, MeO substituted phenyl) | H |
| 77 | 4-(2-methoxyethoxy)phenyl (MeO-CH₂CH₂-O-C₆H₄-) | H |
| 78 | 6-aminopyridin-3-yl (H₂N-pyridyl) | H |
| 79 | 6-aminopyridin-3-yl (H₂N-pyridyl) | CH₂CH₂CN | or their pharmaceutically acceptable salts.

4. The compound of claim 2 wherein R¹ represents hydrogen or cyano-lower alkyl.

5. The compound of claim 4 wherein the compounds are selected from the group consisting of the compounds 6, 15, 29, 42, 44, 45, 46, 47, 48, 50, 54, 56, 58, 61, 64, 65, 70, 78 and 79, which compounds are set forth according to the following table:

| Compound | R | R¹ |
|---|---|---|
| 6 | 4-chlorophenyl | CH₂CH₂CN |
| 15 | 3,4-dimethoxyphenyl (MeO, MeO substituted phenyl) | H |
| 29 | 4-bromophenyl | H |
| 42 | naphthalen-2-yl | H |
| 44 | 4-methylphenyl | H |
| 45 | benzo[1,3]dioxol-5-yl | H |
| 46 | naphthalen-2-yl | CH₂CH₂CN |
| 47 | 4-bromophenyl | CH₂CH₂CN |
| 48 | 4-methoxyphenyl | CH₂CH₂CN |

-continued

| Compound | R | R¹ |
|---|---|---|
| 50 | 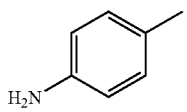 | H |
| 54 | 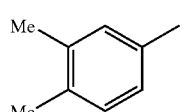 | CH₂CH₂CN |
| 56 | 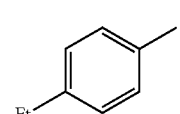 | CH₂CH₂CN |
| 58 | 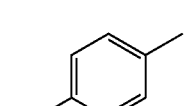 | CH₂CH₂CN |
| 61 | 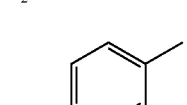 | CH₂CH₂CN |
| 64 | 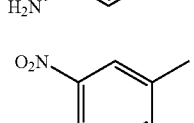 | H |
| 65 | 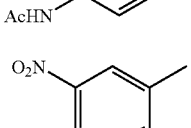 | H |
| 70 | 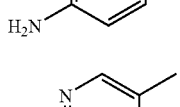 | H |
| 78 | 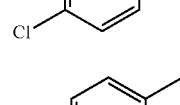 | H |
| 79 | 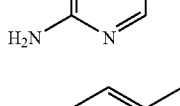 | CH₂CH₂CN | or their pharmaceutically acceptable salts.

6. The compound of claim 2, wherein R is optionally substituted phenyl.

7. The compound of claim 6 wherein said compound is 4-[1-(4-aminophenacyl)-1H-benzimidazol-2-yl]-furazan-3-yl-N-(2-cyanoethyl)-amine or pharmaceutically acceptable salts thereof.

8. The compound of claim 4 where the compound has the formula

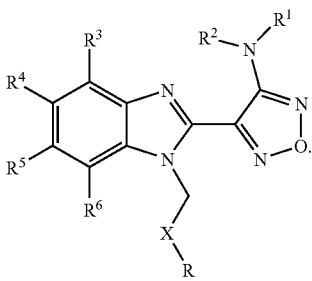

wherein
R is pyridinyl optionally substituted in one or two positions by lower alkoxy, amino, or halogen;
X is —C=Y; Y is oxygen;
R¹ is cyano-lower alkyl or hydrogen and;
R², R³, R⁴, R⁵, R⁶ is hydrogen;
or a pharmaceutically acceptable salt thereof.

9. The compound of claim 8 wherein R¹ is cyano-lower alkyl.

10. The compound of claim 9 wherein said compound is 4-[1-(6-amino-3-pyridylcarbonylmethyl)-1H-benzimidazol-2-yl]-furazan-3-yl]-N-(2-cyanoethyl)-amine or its pharmaceutical acceptable salts.

11. The compound of claim 8 wherein R¹ is hydrogen.

12. The compound of claim 11 wherein said compound is 4-[1-(6-amino-3-pyridylcarbonylmethyl)-1H-benzimidazol-2-yl]-furazan-3-ylamine; or pharmaceutical acceptable salts thereof.

13. The compound of claim 6 where said compound has the formula

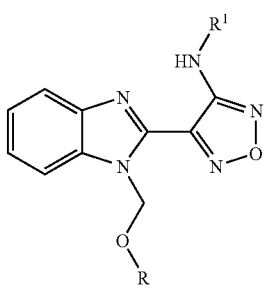

which compound is selected from the group consisting of the compounds 7, 10, 88, 89, 92, 93, 94, 95, 96, 97, 101 and 103, which compounds are set forth according to the following table:

| Compound | R | R¹ |
|---|---|---|
| 7 | 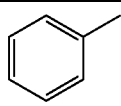 | H |
| 10 | 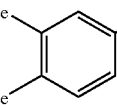 | CH₂CH₂CN |

-continued

| Compound | R | R¹ |
|---|---|---|
| 88 | 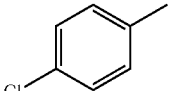 4-Cl-phenyl | H |
| 89 | 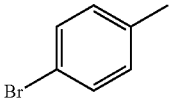 4-Br-phenyl | H |
| 92 | 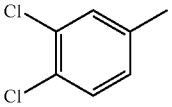 3,4-diCl-phenyl | H |
| 93 | 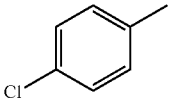 4-Cl-phenyl | CH₂CH₂CN |
| 94 | 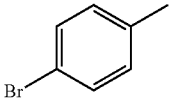 4-Br-phenyl | CH₂CH₂CN |
| 95 | 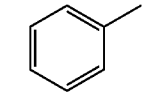 phenyl | CH₂CH₂CN |
| 96 | 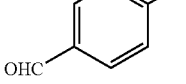 4-CHO-phenyl | H |
| 97 | 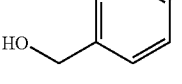 4-CH₂OH-phenyl | H |
| 101 | 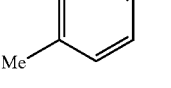 3,4-diMe-phenyl | H |
| 103 | 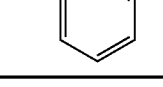 3-CF₃-phenyl | H | or pharmaceutically acceptable salts thereof.

14. The compound of claim 13, which compound is selected from the group consisting of the compounds 89, 92, 94 and 101, which compound are set forth according to the following table:

| Compound | R | R¹ |
|---|---|---|
| 89 | 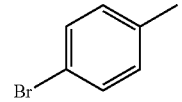 4-Br-phenyl | H |
| 92 | 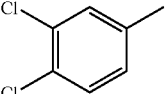 3,4-diCl-phenyl | H |
| 94 | 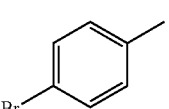 4-Br-phenyl | CH₂CH₂CN |
| 101 | 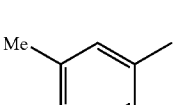 3,4-diMe-phenyl | H | or their pharmaceutically acceptable salts.

15. A compound of the formula (I)

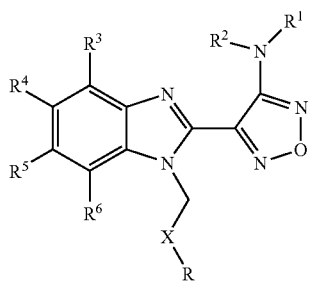

wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen a heterocyclyl, lower alkylcarbonyl, carboxy, lower alkoxycarbonyl, formyl, cyano, halogen, and nitro; and wherein two adjacent substituents are methylenedioxy; and wherein pyridinyl is optionally substituted by lower alkoxy, amino or halogen;

X is —C═Y and Y is nitrogen substituted by an alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy; or pharmaceutically acceptable salts thereof.

16. The compound of claim 15, which compound is selected from the group consisting of the compounds 18 and 22, which compounds are set forth according to the following table:

| Compound | R | R¹ |
|---|---|---|
| 18 | phenyl | H |
| 22 | 4-chlorophenyl | H | or their pharmaceutically acceptable salts.

17. A compound selected from the group consisting of Compound 9 and 13, which compounds are as represented by the following formula and are set forth according to the following table:

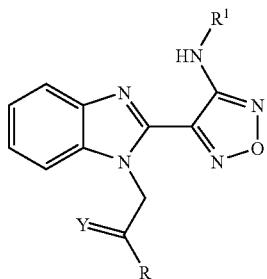

wherein Y is oxygen

| Compound | R | R¹ |
|---|---|---|
| 9 | 4-chlorophenyl | $CH_2CH_2(CO)OCH_3$ |
| 13 | 4-aminophenyl | $CH_2CH_2(CO)OH_3$ | or their pharmaceutically acceptable salts.

* * * * *

UNITED STATES PATENT AND TRADEMARK OFFICE
CERTIFICATE OF CORRECTION

PATENT NO. : 7,385,061 B2  Page 1 of 1
APPLICATION NO. : 10/557539
DATED : June 10, 2008
INVENTOR(S) : Martin Eberle et al.

It is certified that error appears in the above-identified patent and that said Letters Patent is hereby corrected as shown below:

In column 76, line 25 (claim 17, line 8), please change "$CH_2CH_2(CO)OH_3$" to read --$CH_2CH_2(CO)OH$--

Signed and Sealed this

Twenty-third Day of September, 2008

JON W. DUDAS
*Director of the United States Patent and Trademark Office*